(12) United States Patent
Hauser

(10) Patent No.: US 7,879,821 B2
(45) Date of Patent: Feb. 1, 2011

(54) METHOD FOR MODULATING INFLAMMATORY RESPONSES BY ALTERING PLASMA LIPID LEVELS

(75) Inventor: Carl J. Hauser, Boston, MA (US)

(73) Assignee: University of Medicine and Dentistry of New Jersey, Somerset, NJ (US)

( * ) Notice: Subject to any disclaimer, the term of this patent is extended or adjusted under 35 U.S.C. 154(b) by 0 days.

(21) Appl. No.: 11/627,891

(22) Filed: Jan. 26, 2007

(65) Prior Publication Data

US 2008/0032925 A1 Feb. 7, 2008

Related U.S. Application Data

(60) Provisional application No. 60/762,952, filed on Jan. 26, 2006.

(51) Int. Cl.
*A61K 31/724* (2006.01)
*A61K 38/38* (2006.01)
*A61K 31/397* (2006.01)

(52) U.S. Cl. .............. 514/58; 514/12; 514/182; 514/210.02; 424/9.1

(58) Field of Classification Search .............. 514/12, 514/182, 58, 210.02; 424/9.1
See application file for complete search history.

(56) References Cited

U.S. PATENT DOCUMENTS

2005/0282734 A1 * 12/2005 Kadima et al. ............ 514/2

FOREIGN PATENT DOCUMENTS

WO WO 99/49896 * 10/1999

OTHER PUBLICATIONS

Davis et al. , Arterscler Thromb. Vasc. Biol. 21, 2032-2038 (2001).*

\* cited by examiner

*Primary Examiner*—Chih-Min Kam
(74) *Attorney, Agent, or Firm*—Fox Rothschild LLP

(57) ABSTRACT

A method for treating an immune-related disorder in a patient comprising administering an agent to the patient for altering the patient's plasma concentration of free cholesterol, wherein said agent is a non-statin agent and is administered in an amount sufficient to modulate the immune-related disorder.

5 Claims, 27 Drawing Sheets

METHOD FOR MODULATING INFLAMMATORY RESPONSES BY ALTERING PLASMA LIPID LEVELS

CROSS REFERENCE TO RELATED APPLICATIONS

This application claims priority to U.S. Provisional Application Ser. No. 60/762,952, which was filed on Jan. 26, 2006, the disclosure of which is incorporated herein by reference.

STATEMENT REGARDING FEDERALLY SPONSORED RESEARCH

The U.S. Government has a paid-up license in this invention and the right in limited circumstances to require the patent owner to license others on reasonable terms as provided for by the terms of grant 2 R01 GM059179 awarded by the National Institutes of Health.

BACKGROUND OF THE INVENTION

Cholesterol causes hardening of the arteries, but for unknown reasons this mostly occurs in patients with inflammation. Cholesterol is a major component of lipid rafts, which are areas on cell surfaces that concentrate signaling molecules. These signals include calcium entry into cells, which activates white blood cells and causes inflammation.

Many inflammatory cell responses are tightly controlled by the regulated entry of $Ca^{2+}$ ions into the cell. Because innate immune cells lack voltage-gated calcium channels, processes like chemotaxis, phagocytosis, respiratory burst and degranulation in response to G-protein coupled (GPC) mediators depend in great measure on store-operated calcium entry (SOCE) into the cell. SOCE is the second phase of a biphasic, agonist-activated $Ca^{2+}$ mobilization mechanism that is found in essentially all "non-excitable" eukaryotic cells. This process is initiated when GPC receptors linked to Gi or Gq, or when receptor tyrosine kinases that couple to phospholipases activate Phospholipase C (PLC). PLC breaks down PIP2 to inositol (1,4,5) triphosphate (InsP3) and diacylglycerol. InsP3 diffuses to the endoplasmic reticulum where it depletes InsP3-sensitive calcium stores and thus activates SOCE.

Diacylglycerol also has the intrinsic capacity to activate calcium entry channels. Thus in fact, total "stimulated calcium entry" in native cells is probably the additive result of several processes including store depletion that can initiate $Ca^{2+}$ channel gating. This is clearly the case in the neutrophil (PMN). The complex group of mechanisms by which calcium entry is stimulated is still poorly understood. Nonetheless, as disclosed in Itagaki et al., "Sphingosine 1-phosphate, a diffusible calcium influx factor mediating store-operated calcium entry," *J. Biol. Chem.*, 278(30), 27540-7 (2003), sphingosine 1-phosphate (S1P) acts in the PMN as a second messenger, and links GPC store depletion to $Ca^{2+}$ entry. It was further shown in Itagaki et al., "Lysophosphatidic acid triggers calcium entry through a non-store-operated pathway in human neutrophils," *J. Leukoc. Biol.*, 181-9 (2005) [e-pub., Nov. 2, 2004] that related lysophospholipids, like lysophosphophatidic acid (LPA), act similarly in PMN and other systems. The mechanisms by which S1P and related lysophospholipids gate calcium entry into cells, however, remain entirely unknown, so that a means by which calcium entry can be regulated to modulate inflammatory cell response is also not understood.

SUMMARY OF THE INVENTION

An explanation of these mechanisms is provided herein. We found extra-cellular cholesterol rapidly incorporated into rafts. This moved calcium pores into the rafts, allowing calcium to enter the cell and activating inflammation. The amount of cholesterol in the rafts appears to govern this process. Cholesterol, inflammation and atherosclerosis are linked because raft cholesterol content alters cell signaling.

We have discovered novel pathways by which specific lipids interact to modify the structure and function of inflammatory cells. Interventions in these pathways enable the creation of novel approaches to the therapy of a wide variety of immune-related disorders. Therefore, in accordance with the present invention, a method is provided for treating an immune-related disorder in a patient by administering an agent to the patient for altering the patient's plasma concentration of free cholesterol, wherein the agent is a non-statin agent and is administered in an amount sufficient to modulate the immune-related disorder.

The agent may decrease or increase the patient's plasma concentration of free cholesterol by an amount sufficient to modulate the immune-related disorder. In one embodiment, the immune-related disorder is caused by a hyperimmune or autoimmune response in the patient and the agent will decrease the patient's plasma concentration of free cholesterol by an amount effective to modulate the hyperimmune or autoimmune response. In another embodiment, the immune-related disorder is caused by a hypoimmune response in the patient, and the agent will increase the patient's plasma concentration of free cholesterol by an amount effective to modulate the hypoimmune response.

In one hyperimmune or autoimmune embodiment, the agent comprises methyl-β cyclodextrin, lipid-free albumin, or ezetimibe. A statin may also be used in combination with methyl-β cyclodextrin. In one hypoimmune embodiment, the agent comprises free cholesterol, cholesterol-saturated albumin or cholesterol mixtures with lysophospholipids or sphingolipids, either in free or in albumin-saturated forms. In additional embodiments, the agent may enhance or inhibit the activity of an enzyme involved in the metabolism of the free cholesterol to increase or decrease the patient's plasma concentration of free cholesterol. Lowering the activity of free cholesterol by binding it with lipid-free albumin or other binding agents might also be used in combination with the above interventions.

The immune-related disorder may comprise a hyperimmune or autoimmune-related disorder such as, for example, systemic inflammation after trauma, injury or sepsis, transplant, transplant rejection, atherosclerosis, neointimal hyperplasia, rheumatoid arthritis, inflammatory bowel disorders, such as, celiac disease, irritable bowel syndrome, ulcerative colitis, Addison's disease, and the like. Further, if Alzheimer's disease is shown to be a hyperimmune or autoimmune disorder, as some presently theorize, the inventive method could also be used to slow down or halt the progression of this disease.

In another embodiment, the agent is administered from 2 to 10 days following bodily shock or injury to the patient or following sepsis, at which times plasma concentrations of cholesterol are typically depressed and the patient's immune responses are also suppressed. Chronic diseases such as cirrhosis which are associated with hypocholesterolemia and manifest a predisposition to sepsis may also be treated by these methods. The agent may be administered to the patient orally or parenterally. The agent may further comprise a pharmaceutically acceptable carrier. A pharmaceutical composition comprising free cholesterol and a pharmaceutically acceptable carrier such as albumin is also provided in accordance with the present invention.

DETAILED DESCRIPTION OF THE INVENTION

Lipid rafts are sphingolipid- and cholesterol-enriched planar domains of the cell membrane. Rafts play key roles in a variety of cell signaling processes by virtue of acting as 'staging areas' for the assembly of molecular signaling complexes. Moreover, human transient receptor protein 1 (TRPC1) is associated with lipid raft domains and changes in TRPC1 localization are involved with the regulation of PMN SOCE, as described in Itagaki et al., "Cytoskeletal reorganization internalizes multiple TRP channels and blocks calcium entry into human neutrophils," *J. Immunol.*, 172, 601-607 (2004).

Figure 3:
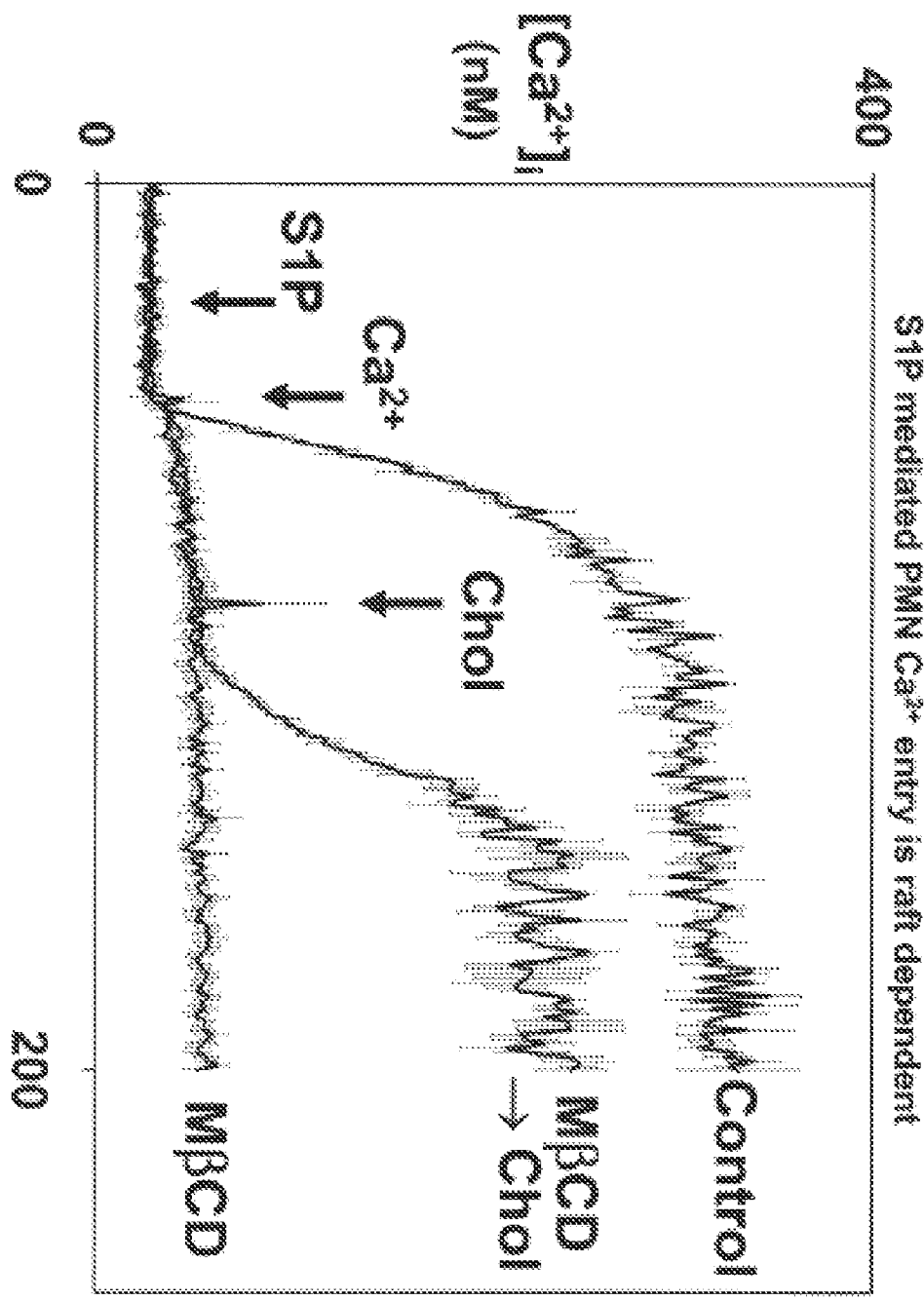
FIG. 3 demonstrates that S1P mediated PMN Ca entry is raft dependent.

S1P initiated SOCE has been found to be highly dependent upon lipid rafts in PMN (FIG. 3). Specifically, the disruption of rafts by sequestering cholesterol using methyl-β cyclodextrin (MβCD) completely blocks calcium entry into the cells. This effect is dose dependent and reversible by cholesterol replacement.

Figure 2:
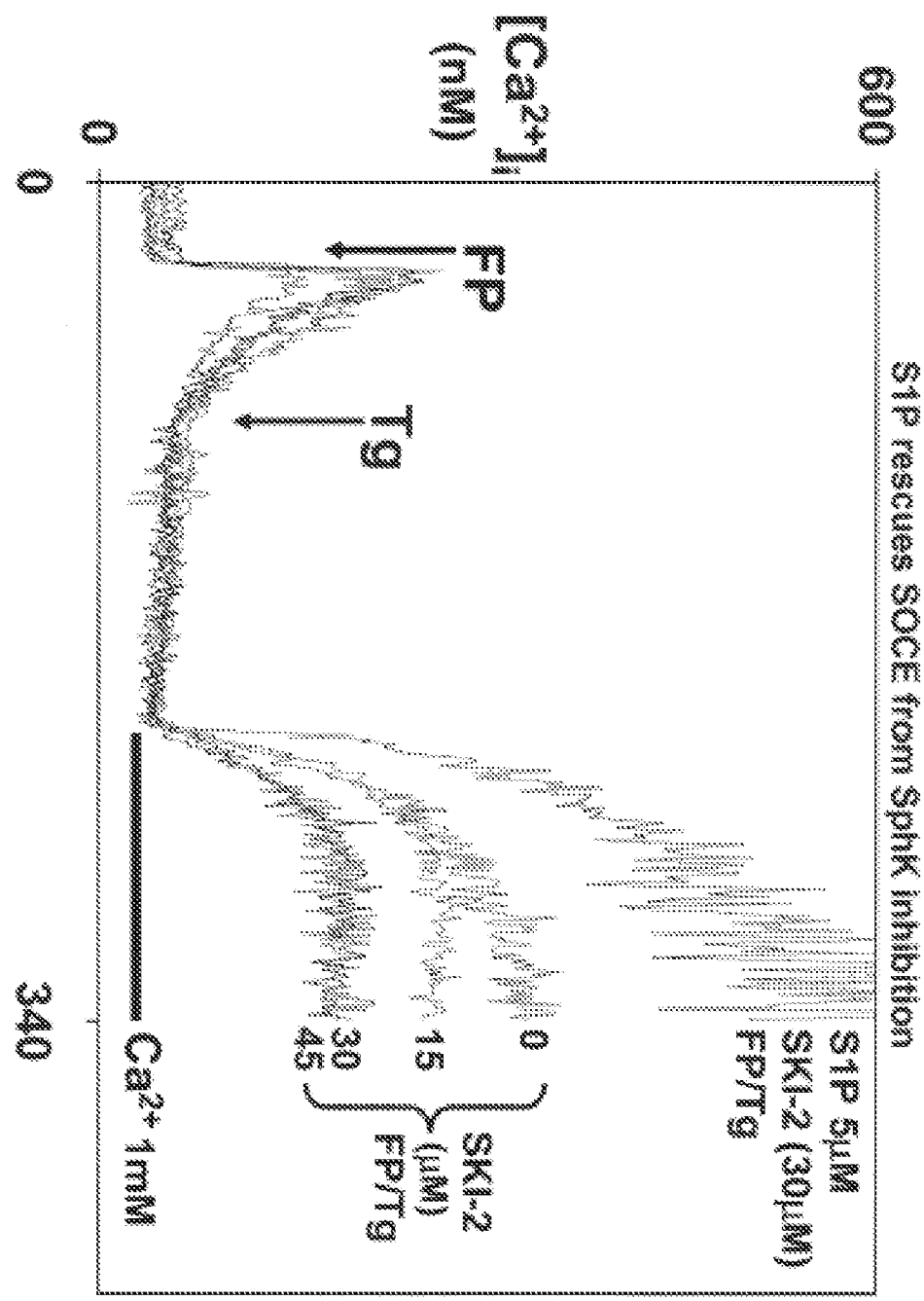
FIG. 2 illustrates that S1P rescues SOCE from SphK inhibition.

Furthermore, PMN $Ca^{2+}$ entry (SOCE) responses to formyl-met-leu-phe (FP) and thapsigargin (Tg) are inhibited by a sphingosine kinase inhibitor (SKI-2) that blocks endogenous S1P synthesis (FIG. 2). This effect is totally reversed by restoration of exogenous S1P to the system.

Figure 1:
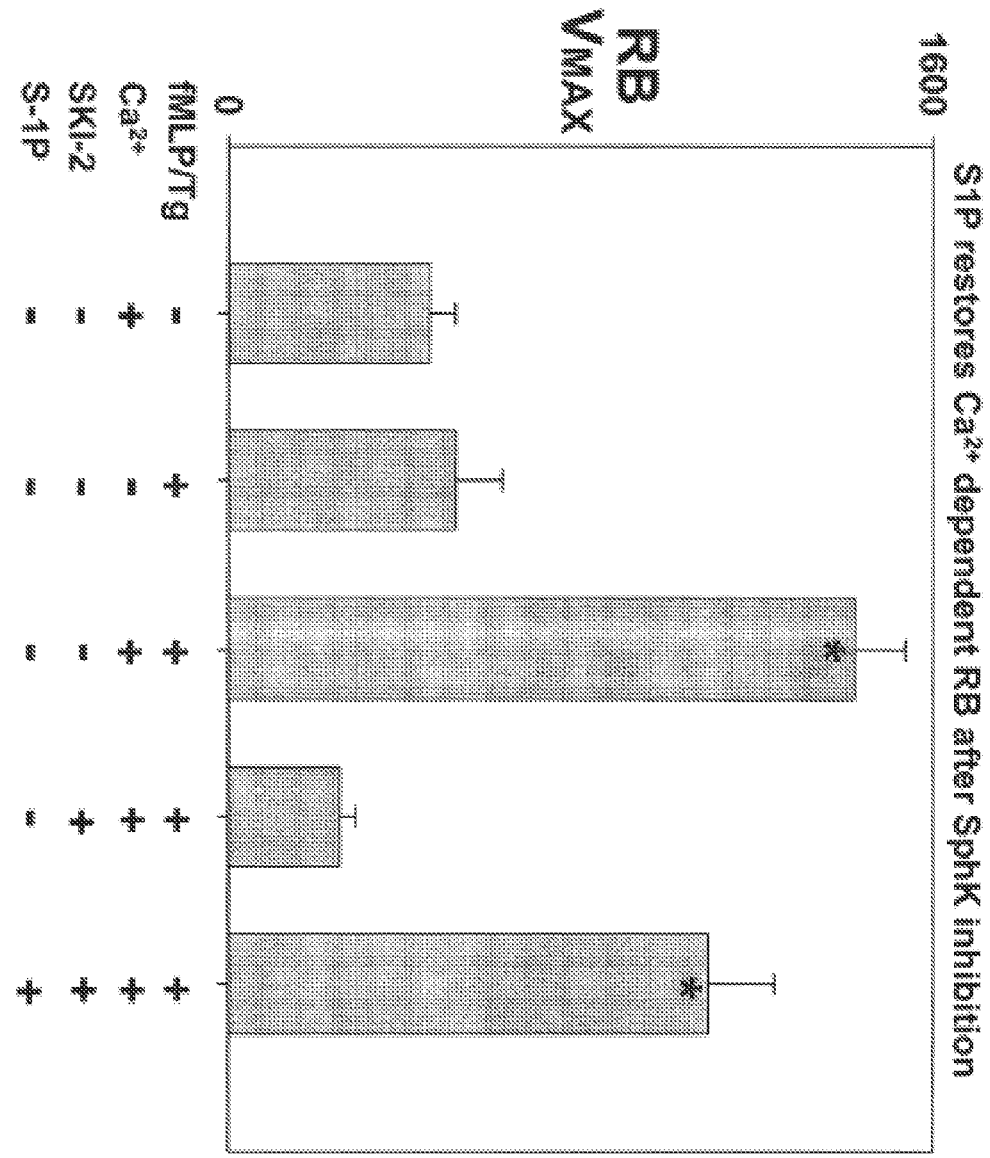
FIG. 1 illustrates that S1P restores $Ca^{2+}$ dependent RB after SphK inhibition.
Figure 21:
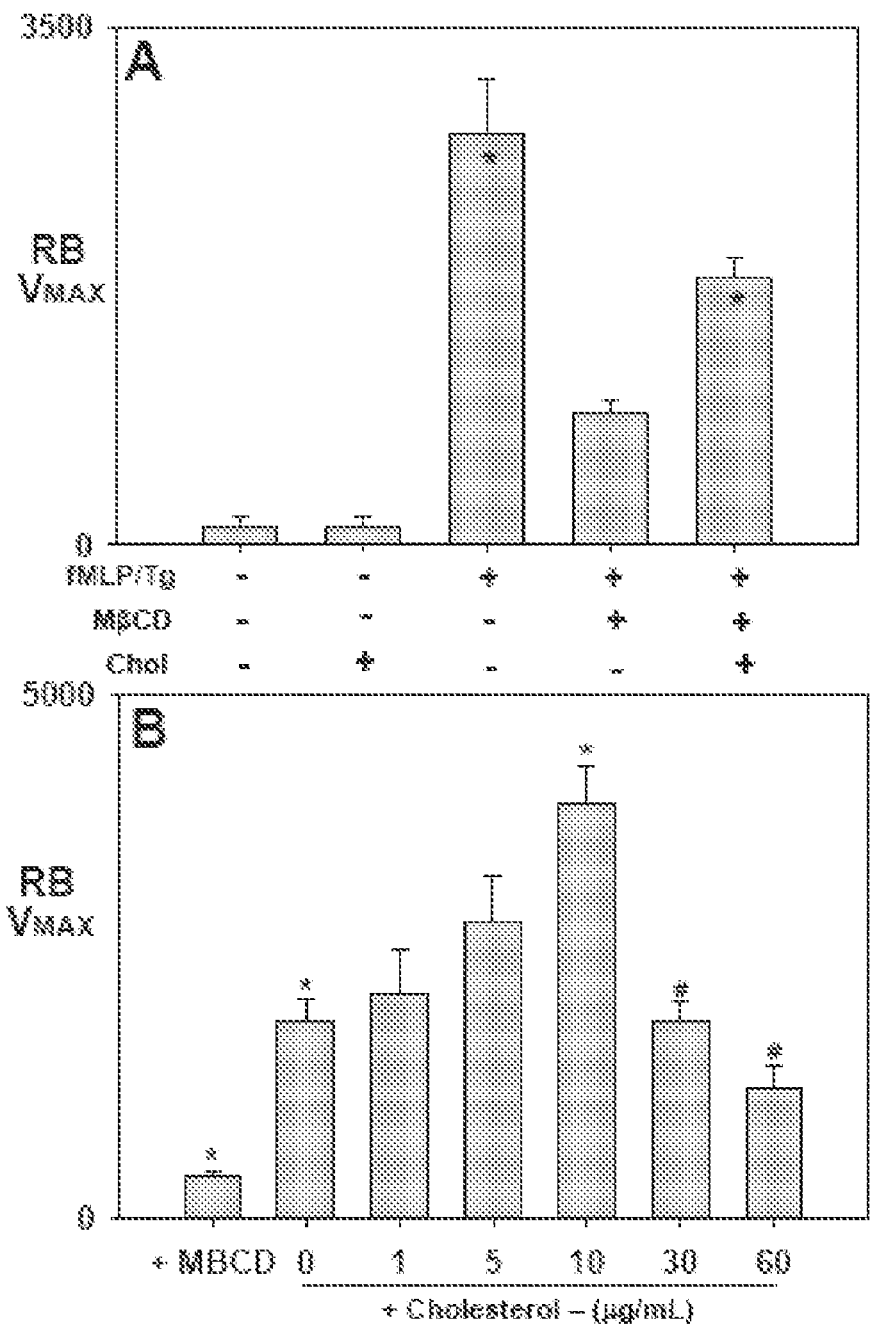
FIGS. 21 A and 21 B demonstrate that cholesterol restores $Ca^{2+}$ dependent RB after raft disruption.

In the identical system, we then showed that a crucial $Ca^{2+}$-entry dependent inflammatory cellular function (respiratory burst, RB) was inhibited by either inhibition of S1P synthesis using SKI-2 (FIG. 1) or by MβCD (FIG. 21). Again, these effects were reversed by exogenous S1P and cholesterol restoration.

These findings led us to hypothesize that cholesterol might have a direct effect upon $Ca^{2+}$ entry via raft-dependent signal mechanisms, as well as via S1P-dependent raft trafficking. We therefore studied whether cholesterol could directly gate calcium entry into PMN (FIG. 19).

We found that free cholesterol (i.e. in the absence of albumin) was a potent, dose-dependent activator of cellular $Ca^{2+}$ entry in the PMN. These effects also occur in the presence of albumin, but require longer exposures. This $Ca^{2+}$ entry was inhibited by lanthanides, demonstrating that it occurs through a cationic channel mechanism. This understanding of the mechanisms linking cholesterol and inflammation is completely novel and vital to our understanding of a variety of important disease processes including inflammation and atherosclerosis.

Figure 19:
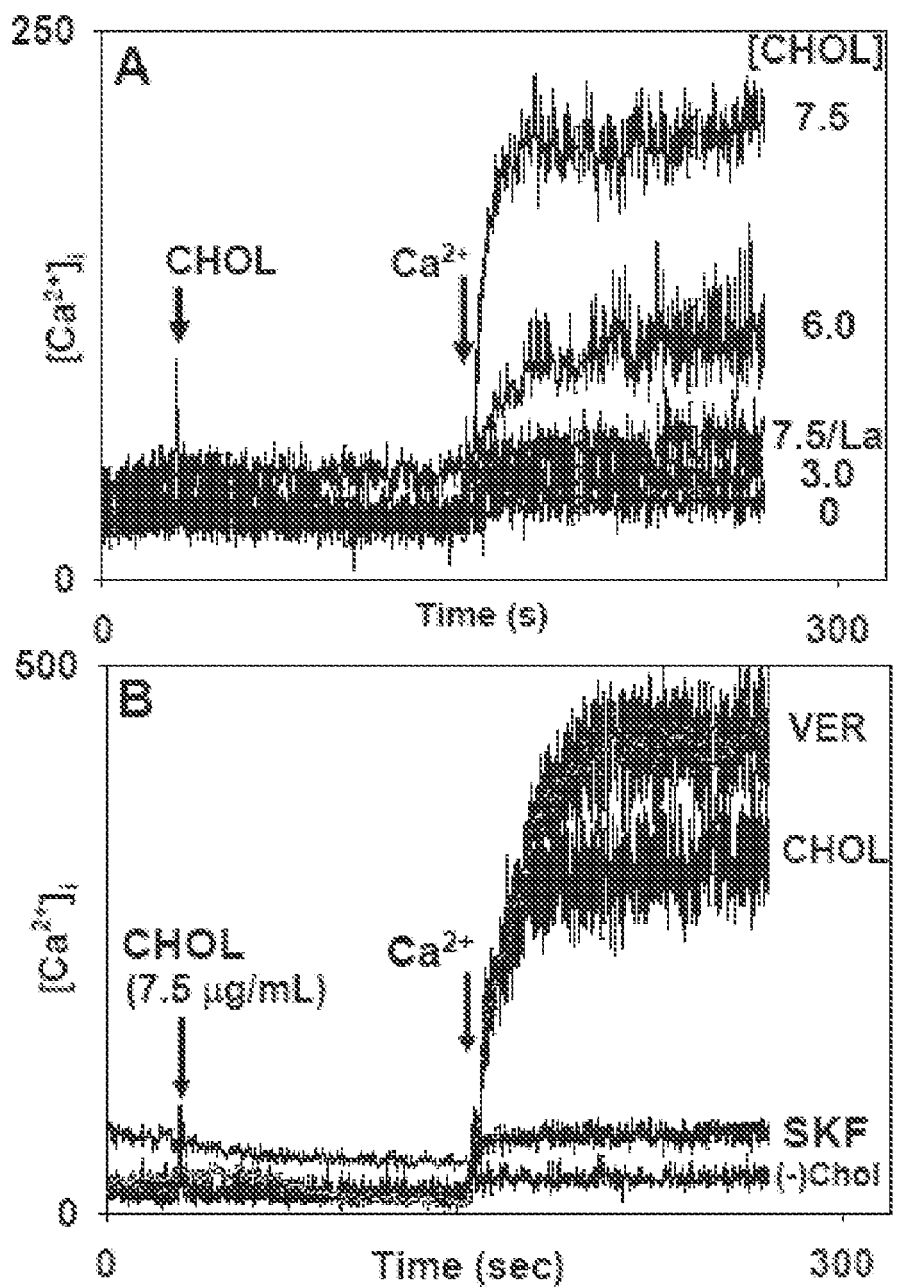
FIG. 19A shows that cholesterol stimulates dose-dependent $Ca^{2+}$ influx.
FIG. 19B shows that cholesterol-incorporation mediated $Ca^{2+}$ entry was sensitive to the non-specific dihydropyridine SKF96365.

Further inhibitor experiments showed that these channels were not inhibited by the L-type calcium channel blocker verapamil, but were inhibited by non-specific cationic channel blocker SKF96365 (FIG. 19). These findings confirm the crucial discovery that cholesterol interacts with sphingolipids in rafts to gate immune cell calcium entry through activation of non-specific cationic channels. These channels are probably of the TRPC type crucial for PMN SOCE.

Figure 4:
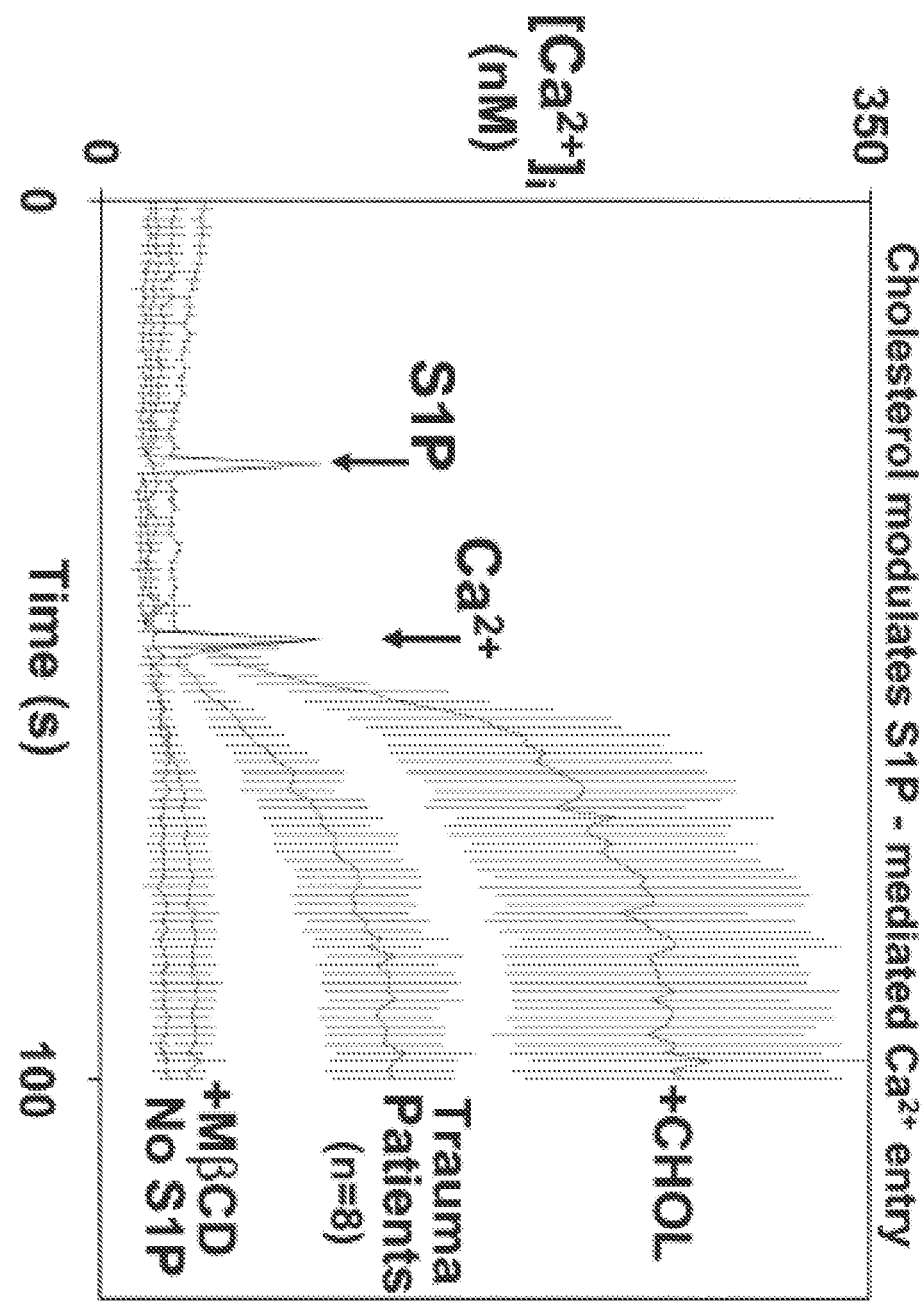
FIG. 4 demonstrates that cholesterol modulates SIP-mediated $Ca^{2+}$ entry.

Subsequent to these experiments, we have assessed whether these findings can be applied to modulation of the responsiveness of immune cells both in normal volunteers and in injured patients. We find that PMN $Ca^{2+}$ entry responses to S1P are depressed after injury. Further though, we find that these responses can be further suppressed by MβCD and restored to healthy volunteer levels by exogenous application of cholesterol to the system (FIG. 4).

These findings demonstrate that manipulation of the cholesterol and lysophospholipids in cellular environments can be used as a means of altering the basic signaling processes that activate immune cells.

Figure 14:
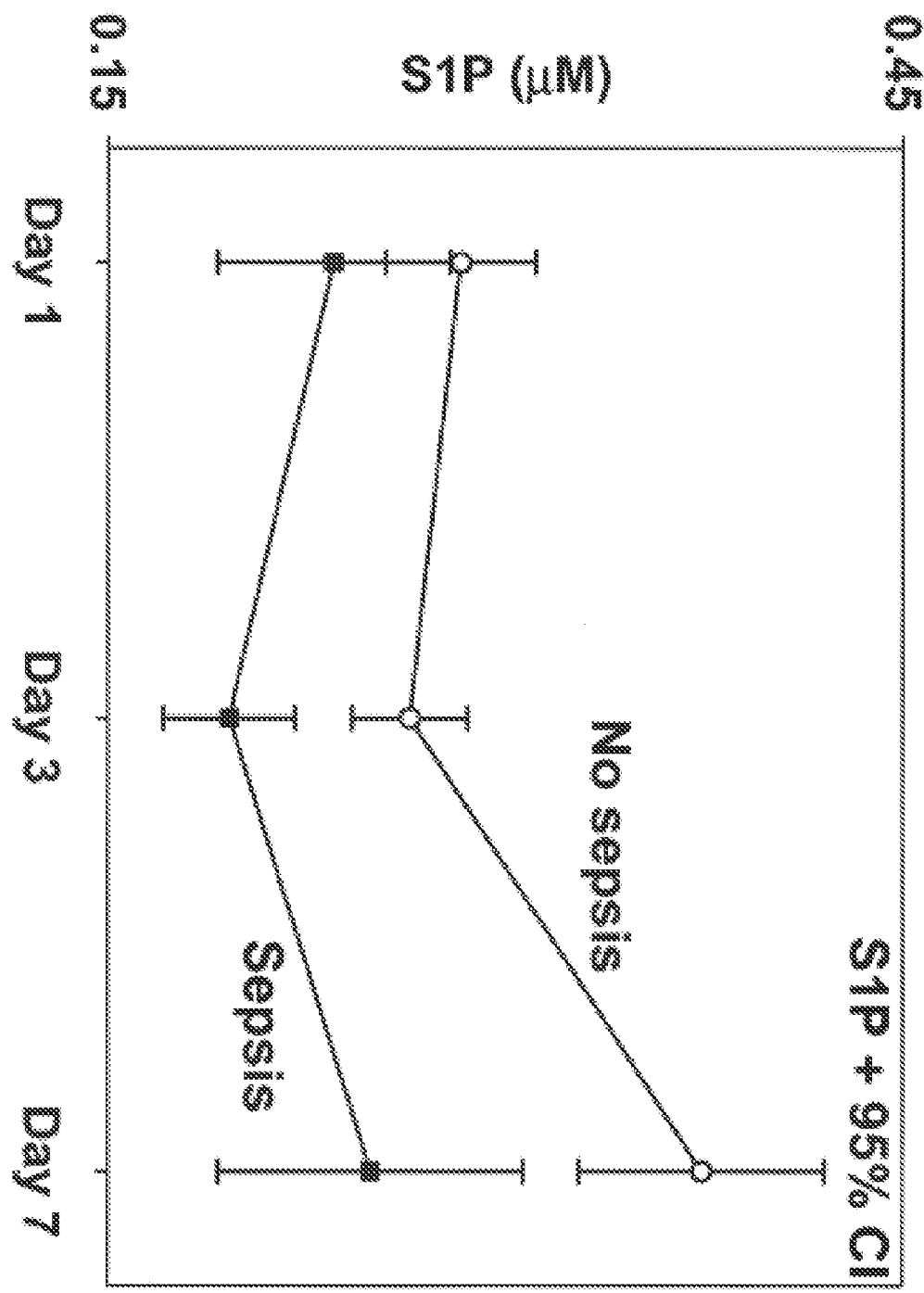
FIG. 14 is a graph of trauma patient plasma S1P levels as a function of time.

To determine the clinical relevance of these findings, we evaluated a large group of prospectively collected trauma patient plasma samples. This revealed that plasma SIP levels are suppressed during the initial week after injury, when patients are at highest risk for sepsis (FIG. 14). Moreover, suppression of S1P levels was markedly greater in patients who developed sepsis than in those who do not. Patients who had plasma levels of S1P <0.3 µM on admission (i.e. decreased more than 1 standard deviation [S.D.] from matched volunteer plasma levels) had a median ICU length of stay of 11 days. Patients whose S1P levels were within 1 S.D. of 'normal' levels spent a median 4 days in the ICU. These data suggest S1P is critically important in the immune surveillance of sepsis.

Figure 15:
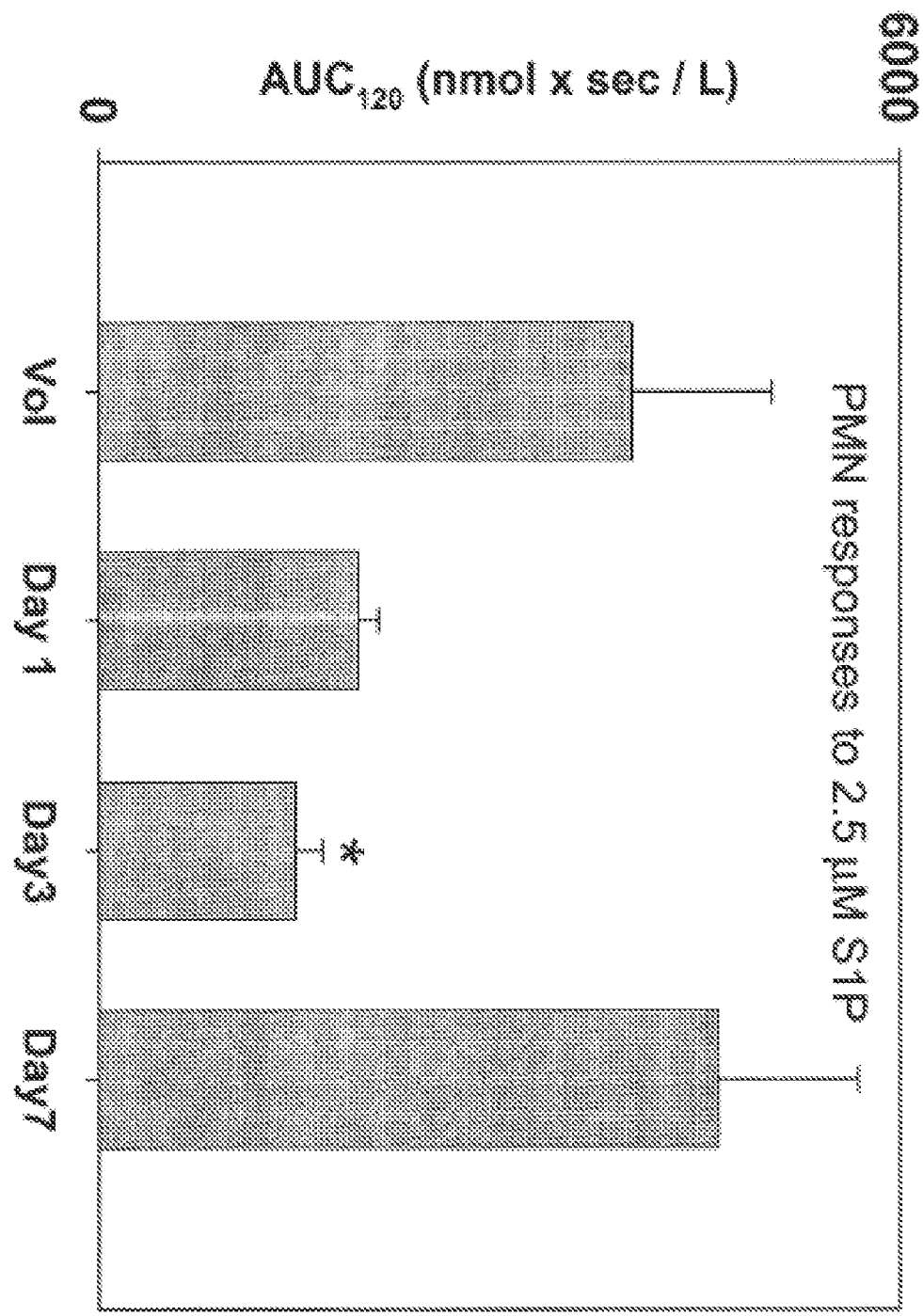
FIG. 15 is a graph illustrating trauma patient PMN responses to 2.5 M S1P.

But trauma patients not only had lower levels of circulating S1P, their PMN also have less active responses to S1P. FIG. 15 shows that neutrophils (PMN) mobilize less calcium on exposure to S1P than do volunteer PMN. This effect dissipates over the week after injury as patients recover. These data again, suggest S1P mediated calcium entry, which is cholesterol dependent, is critically important in the immune surveillance of sepsis. But moreover, diminished responses to S1P in the presence of a diminished plasma concentration of S1P suggest that an additive, physical-chemical mechanism exists for S1P effect rather than an enzymatic or receptor-based mechanism.

Figure 16:
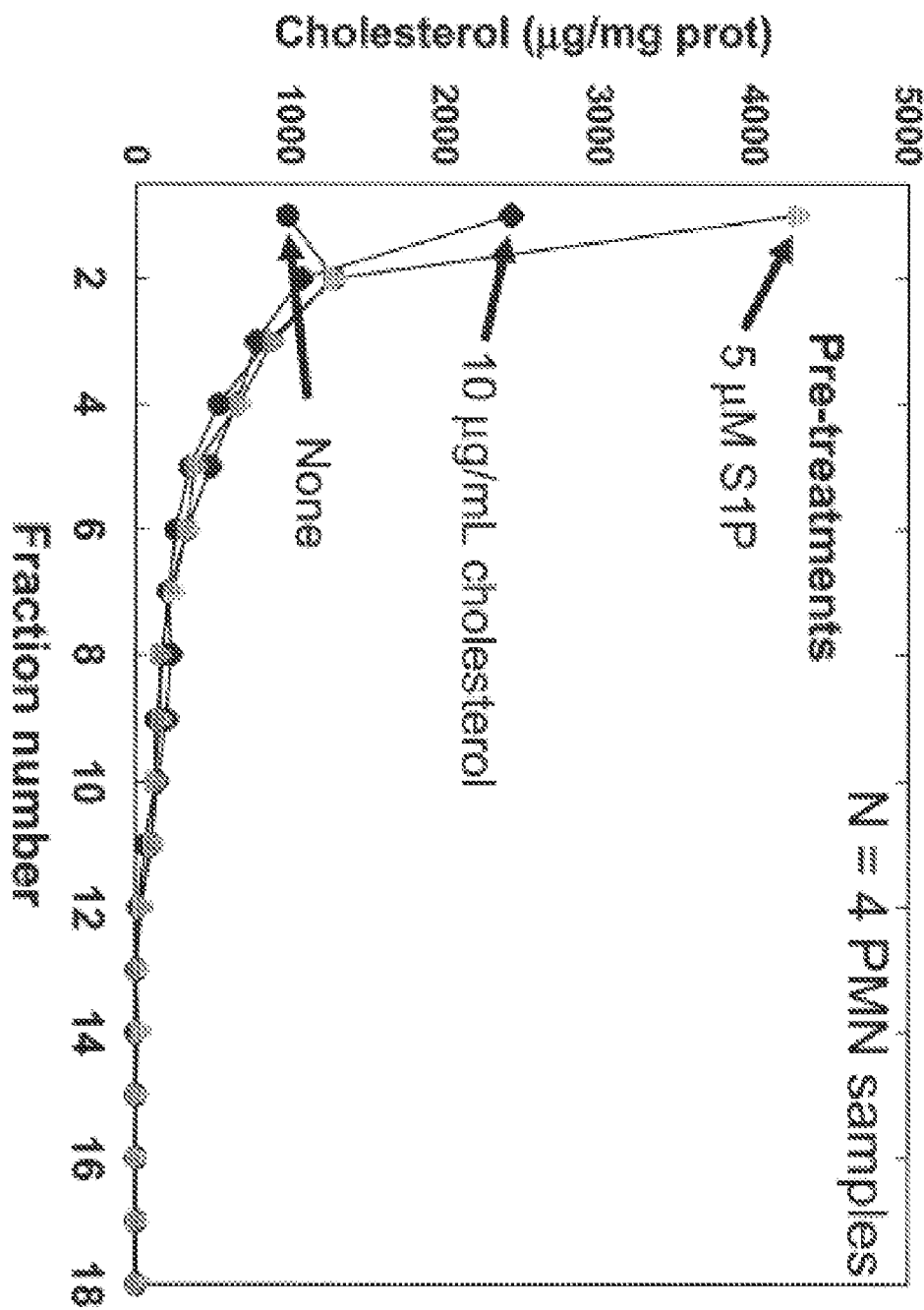
FIG. 16 is a graph showing that treatment of PMN with micromolar concentrations of cholesterol (in the absence of albumin) more than doubles the ratio of cholesterol to protein in the lowest density raft fractions.

Because both cholesterol and sphingolipids are well known to be key components of the lipid raft domains which we showed above were intrinsic to inflammatory PMN responses, we isolated lipid raft fractions by ultracentrifugation from PMN treated with S1P or cholesterol or with buffer only. Cholesterol is typically present in plasma in concentrations of grams/liter, but it is highly bound to lipoproteins and albumin. FIG. 16 shows that treatment of PMN with micromolar concentrations of cholesterol (in the absence of albumin) more than doubles the ratio of cholesterol to protein in the lowest density raft fractions. This clearly shows that very low concentrations of "free" cholesterol can be used to alter the composition of lipid rafts quite radically. Of similar interest and importance, PMN treatment with S1P also resulted in increases in cholesterol concentration in the lowest density raft fractions. Thus we see that environmental cholesterol and environmental sphingolipids interact, and can be used to alter lipid raft composition. Finally, as shown in the Figures discussed above, altering lipid raft function in these ways can be used as a method of modulating PMN signaling and ultimately, inflammatory function.

Based upon these discoveries, the present invention thus provides a method for treating an immune-related disorder in a patient comprising administering an agent to the patient for altering the patient's plasma concentration of free cholesterol, wherein said agent is a non-statin agent and is administered in an amount sufficient to modulate the immune-related disorder.

Immune-related disorders include hyperimmune or autoimmune-related disorders such as, for example, systemic inflammation immediately after shock, injury or sepsis, transplant rejection, atherosclerosis, neointimal hyperplasia, rheumatoid arthritis, inflammatory bowel disorders, such as, celiac disease, irritable bowel syndrome, ulcerative colitis, and the like, Addison's disease, Alzheimer's disease, if shown to be a hyperimmune or autoimmune disorder, and the like. Hypoimmune disorders resulting from bodily shock or injury to the patient are also included within the scope of the present invention.

In the case of a hyperimmune or autoimmune-related disorder, the agent is administered such that it decreases the patient's plasma concentration of free cholesterol by an amount sufficient to modulate the immune-related disorder. Suitable agents for this purpose include, for example, methyl-0 cyclodextrin, lipid-free albumin, or agents that inhibit biliary and dietary cholesterol absorption, such as ezetimibe. Alternatively, intravenous administration of proteins like albumin can suppress the activity of free cholesterol by binding it. A statin can also be administered in combination with the agent or agents for decreasing the patient's plasma concentration of free cholesterol. The present invention contemplates co-administration with other agents and methods for treating hyperimmune and autoimmune-related disorders.

In the case of a hypoimmune-related disorder, the agent or agents administered will act so as to increases the patient's plasma concentration of free cholesterol by an amount sufficient to modulate the immune-deficiency related disorder. An effective amount of free cholesterol or cholesterol bound to and saturating a carrier, like albumin, can be administered to the patient for this purpose. Other exemplary agents include sphingolipids and lysophospholipids that may participate with cholesterol in the formation of rafts that can also be used to increase the tendency of free cholesterol to form and stabilize lipid rafts. These might be delivered in oral or parenteral formulations.

Another aspect of the invention involves administering the agent as described above, wherein the agent is provided in a pharmaceutically acceptable carrier. The term "pharmaceutically acceptable carrier" refers to those components in the particular dosage form employed which are inert and are typically employed in the pharmaceutical arts to formulate a particular active compound. This may include without limitation solids or liquids and gases, used to formulate the particular pharmaceutical product. Examples of carriers include diluents, flavoring agents, solubilizers, lubricants, suspending agents, binders or tablet disintegrating agents, encapsulating materials, penetration enhancers, solvents, emollients, thickeners, dispersants, sustained release forms, such as matrices, transdermal delivery components, buffers, stabilizers, preservatives and the like. Each of these terms is understood by those of ordinary skill.

Numerous methods are presently available for administering the pharmaceutical composition to a patient. The agent may be administered locally or systemically, depending upon whether the condition to be treated is systemic or localized. The composition may be introduced parenterally, transmucosally, e.g., orally, nasally, or rectally, or transdermally. Preferably, administration is parenteral, e.g., via intravenous injection, and also includes, but is not limited to, intra-arteriole, intramuscular, intradermal, subcutaneous, intraperitoneal, intraventricular, and intracranial administration. In all cases, because cholesterol and the lysophospholipids are highly albumin bound, parenteral formulations could be based on albumin as a carrier.

The invention described herein also includes the administration of the agent in various pharmaceutical dosage forms. The pharmaceutical dosage forms include those recognized conventionally, e.g. tablets, capsules, oral liquids and solutions, drops, parenteral solutions and suspensions, emulsions, oral powders, inhalable solutions or powders, aerosols, topical solutions, suspensions, emulsions, creams, lotions, ointments, transdermal liquids and the like.

The pharmaceutical dosage forms may include one or more pharmaceutically acceptable carriers. Such materials are non-toxic to the recipients at the dosages and concentrations employed, and include diluents, solubilizers, lubricants, suspending agents, encapsulating materials, penetration enhancers, solvents, emollients, thickeners, dispersants, buffers such as phosphate, citrate, acetate and other organic acid salts, anti-oxidants such as ascorbic acid, preservatives, low molecular weight (less than about 10 residues) peptides such as polyarginine, proteins such as serum albumin, gelatin, or immunoglobulins, other hydrophilic polymers such as poly (vinylpyrrolidinone), amino acids such as glycine, glutamic acid, aspartic acid, or arginine, monosaccharides, disaccharides, and other carbohydrates, including cellulose or its derivatives, glucose, mannose, or dextrines, chelating agents such as EDTA, sugar alcohols such as mannitol or sorbitol, counterions such as sodium and/or nonionic surfactants such as tween, pluronics or PEG.

Subjects in need of treatment, typically mammalian, using the methods of this invention, can be administered drug dosages that will provide optimal efficacy. The dose and method of administration will vary from subject to subject and be dependent upon such factors as the type of mammal being treated, its sex, weight, diet, concurrent medication, overall clinical condition, the particular compounds employed, the specific use for which these compounds are employed, and other factors which those skilled in the medical arts will recognize. The agents used in this invention may be prepared for storage under conditions suitable for the preservation of drug activity and are typically suitable for storage at ambient or refrigerated temperatures.

Aerosol preparations are typically suitable for nasal or oral inhalation, and may be in powder or solution form, in combination with a compressed gas, typically compressed air. Additionally, aerosols may be used topically. In general, topical preparations may be formulated to enable one to apply the appropriate dosage to the affected area once daily, and up to three to four times daily, as appropriate.

Depending upon the particular agent selected, transdermal delivery may be an option, providing a relatively steady delivery of the agent, which is preferred in some circumstances. Transdermal delivery typically involves the use of an agent in solution, with an alcoholic vehicle, optionally a penetration enhancer, such as a surfactant, and other optional ingredients. Matrix and reservoir type transdermal delivery systems are examples of suitable transdermal systems. Transdermal delivery differs from conventional topical treatment in that the dosage form delivers a systemic dose of the therapeutic agent to the patient.

The agent may also be administered in the form of liposome delivery systems, such as small unilamellar vesicles, large unilamellar vesicles and multilamellar vesicles. Liposomes may be used in any of the appropriate routes of administration described herein. For example, liposomes may be formulated that can be administered orally, parenterally, transdermally, or via inhalation. Drug toxicity could thus be reduced by selective drug delivery to the affected site. For example, if the drug is liposome encapsulated, and is injected intravenously, the liposomes used are taken up by vascular cells and locally high concentrations of the drug could be released over time within the blood vessel wall, resulting in improved drug action. The liposome encapsulated drugs are preferably administered parenterally, and particularly, by intravenous injection.

Liposomes may be targeted to a particular site for drug release. This would obviate excessive dosages that are often necessary to provide a therapeutically useful dosage of a drug at the site of activity, and consequently, the toxicity and side effects associated with higher dosages.

Therapeutically effective dosages may be determined by either in vitro or in vivo methods. For each particular compound of the present invention, individual determinations may be made to determine the optimal dosage required. The range of therapeutically effective dosages will naturally be influenced by the route of administration, the therapeutic objectives, and the condition of the patient. For the various suitable routes of administration, the absorption efficiency must be individually determined for each drug by methods well known in pharmacology. Accordingly, it may be necessary for the therapist to titrate the dosage and modify the route of administration as required to obtain the optimal therapeutic effect. The determination of effective dosage levels, that is, the dosage levels necessary to achieve the desired result, will be within the ambit of one skilled in the art. Typically, applications of compound are commenced at lower dosage levels, with dosage levels being increased until the desired effect is achieved. The release rate of the drug from the formulations of this invention are also varied within the routine skill in the art to determine an advantageous profile, depending on the therapeutic conditions to be treated.

A typical dosage might range from about 0.001 mg/k/g to about 1,000 mg/k/g, preferably from about 0.01 mg/k/g to about 100 mg/k/g, and more preferably from about 0.10 mg/k/g to about 20 mg/k/g. Advantageously, the compounds of this invention may be administered several times daily, and other dosage regimens may also be useful.

In practicing the methods of this invention, the non-statin agent may be used alone or in combination with other therapeutic or diagnostic agents. The agent can be utilized in vivo, ordinarily in mammals such as primates such as humans, sheep, horses, cattle, pigs, dogs, cats, rats and mice, or in vitro.

The present invention is further illustrated by the following examples that teach those of ordinary skill in the art how to practice the invention. The following examples are merely illustrative of the invention and disclose various beneficial properties of certain embodiments of the invention. The following examples should not be construed as limiting the invention as claimed.

EXAMPLES

Example 1

We hypothesized that calcium-entry dependent functions like RB would depend upon S1P synthesis and subsequent S1P interactions with rafts. Thus we developed a calcium-entry dependent RB model where Ca entry was manipulated by sphingosine kinase (SphK) inhibition, which inhibits S1P synthesis in response to internal calcium store release. FIG. 2 depicts the SphK inhibitor SKI-2 suppressing SOCE initiated by fMLP (100 nM) and Tg (1 uM) in a dose dependent fashion. Note that the vast majority of cell $[Ca^{2+}]$ increases are due to calcium influx on re-calcifying the medium. To show specificity, note that 5 M S1P reverses 30 μM SKI-2 inhibition.

Example 2

Using the same system to evaluate respiratory burst (RB), SphK inhibition (SKI-2, 30 uM) also blocked fMLP/Tg induced RB down to background levels. (FIG. 1) Just as with Ca$^{2+}$ entry, we see rescue of RB by S1P (5 uM). n=4; −BSA/+ ca buffer in cuvette. ANOVA P<0.001. All Pairwise Multiple Comparison Procedures (Holm-Sidak method) shows that Columns 3 and 5 are different from all other columns (P<0.01). Column 3 is greater than column 5 (P=0.03). No other paired comparisons were significant. Note that in the absence of external calcium fMLP/Tg does not cause RB.

Example 3

To evaluate whether Ca$^{2+}$-entry responses to S1P were raft dependent, we then disrupted lipid rafts using MBCD to bind raft cholesterol. PMN calcium entry responses to S1P are completely blocked by raft disruption. (FIG. 3) Specificity is shown by reversal of the MβCD effect when cholesterol is replenished. n=3.

Example 4

Since G-coupled (eg PAF-Gq) receptor initiated calcium entry requires S1P synthesis and S1P-mediated Ca$^{2+}$ entry was blocked by raft disruption, we studied whether GPC Ca$^{2+}$ entry required rafts and was restored by cholesterol after raft disruption. FIG. 4 depicts the effect of cholesterol and MBCD on PAF (100 nM) mediated SOCE in human PMN. All experiments done in −BSA/—Ca buffer. N=3 except the DMSO/Chol/PAF n=2. For the "no PAF" blank, MBCD/no-PAF, DMSO/no-PAF controls (not shown) n=1.

PMN were isolated and loaded with Fura2 in BSA+, Ca+ buffer. Cells were washed with −BSA —Ca buffer and incubated with either DMSO or 10 mM MBCD for 10 minutes in the eppendorf tubes. The cells were spun and transferred to cuvettes with −BSA —Ca buffer. PAF at 100 nM final was added at 30 seconds. Calcium was added at 200 s. For the cholesterol re-addition experiments cholesterol (3 ug/ml final) was added to the cuvettes. This is a dose that does not itself cause calcium entry (see the prior diagrams). Cells were pre-incubated 2 min, the experiment was started, PAF was added at t=30 s and calcium at 200 s. For the "blank" cells were pre-warmed, washed in −BSA/—Ca buffer and transferred to cuvettes with −BSA, —Ca buffer. Calcium added at 200 sec. For MBCD/Cholestrerol and DMSO/Cholesterol controls (not shown) treated cells were simply transferred to cuvettes and calcium was added at 200 s.

Example 5

Figure 12:
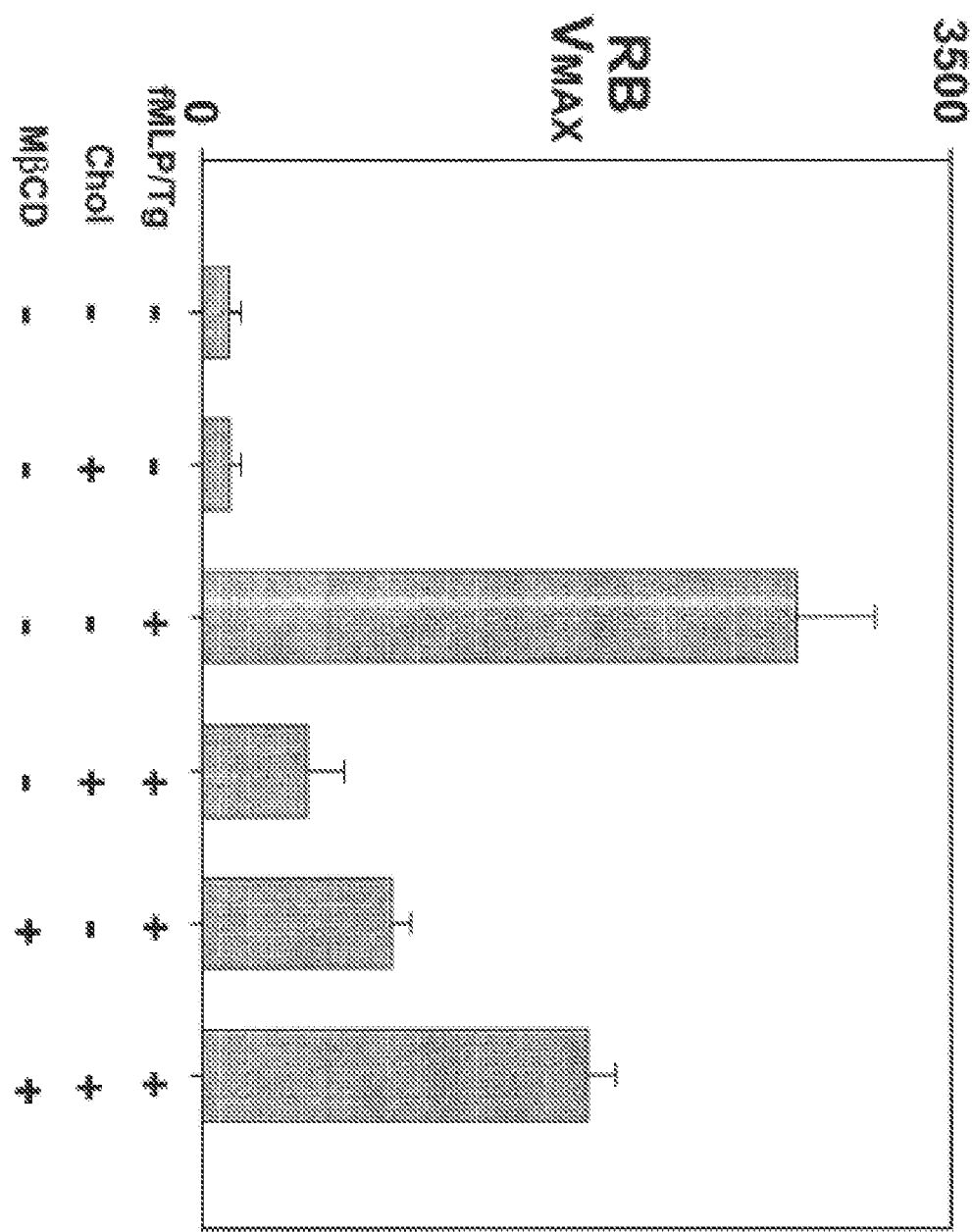
FIG. 12 demonstrates the rescue of calcium-entry dependent respiratory burst by cholesterol (30 ug/ml) on MBCD treated human neutrophils.

Rescue of Calcium-entry dependent respiratory burst by cholesterol (30 ug/ml) on MBCD treated human neutrophils is depicted in FIG. 12. The graph represents Vmax slopes values. n=2 for Blank, Cholesterol Blank and Cholesterol alone. The others are n=6. ANOVA shows P=<0.001, Dunn's all Pairwise Multiple Comparison Procedures showed Column 3 (fMLP/Tg) demonstrated significantly greater RB (*P<0.05) than Columns 1, 2 and 4 but not column 5. Cholesterol depletion attenuated fMLP/Tg initiated, Ca$^{2+}$-entry dependent RB in this model, and subsequent cholesterol restoration significantly rescued that RB.

Example 6

We then assessed PMN responses to S1P in a group of patients, and found that we could modulate PMN calcium entry responses to S1P by varying raft cholesterol content using MbCD and different doses of cholesterol. We found we could actually exceed basal levels of clinical PMN response to S1P with cholesterol (30 ug/ml). n=8 PMN isolates. (FIG. 4)

Example 7

Figure 5:
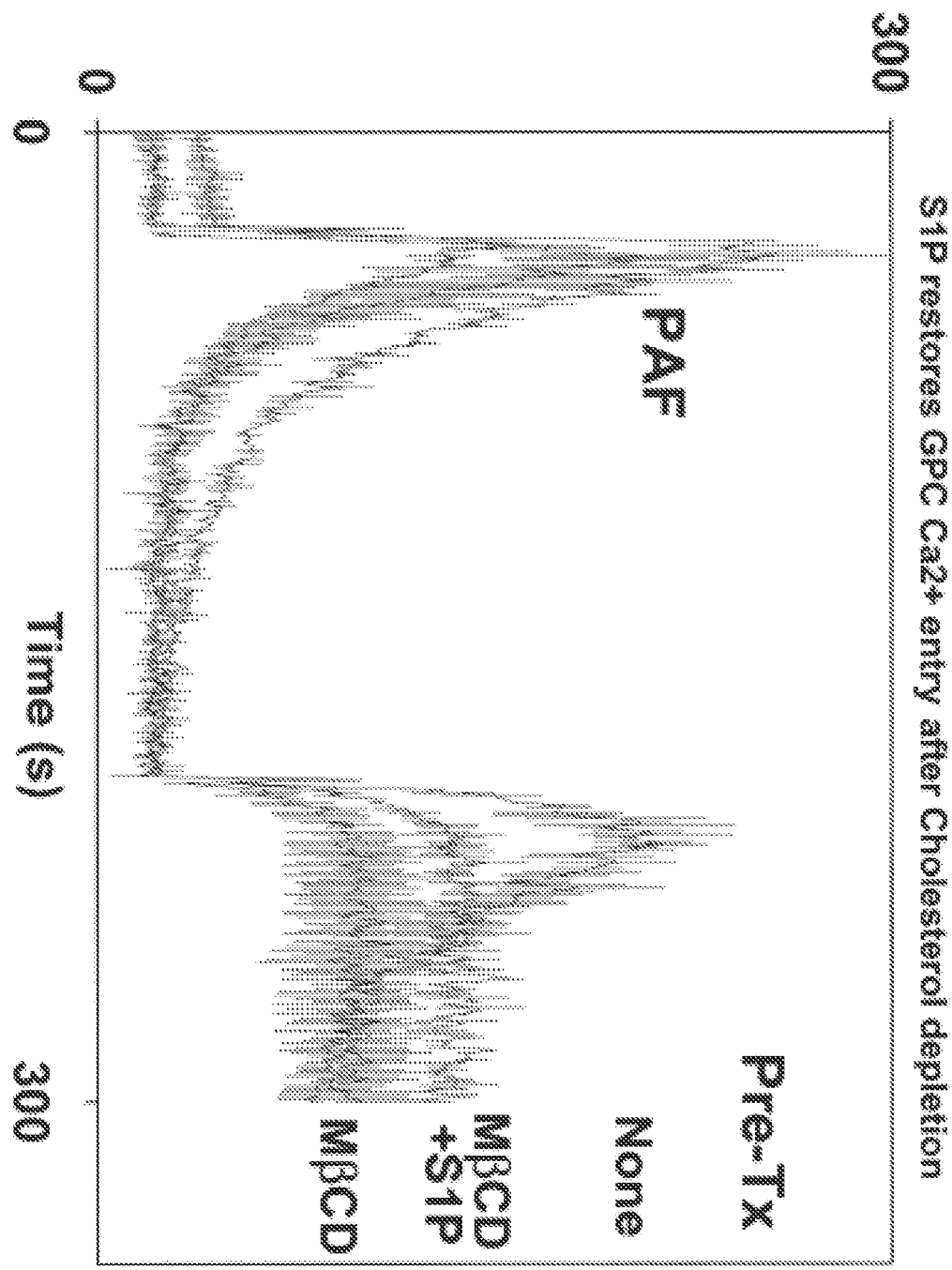
FIG. 5 shows that S1P restores GPC $Ca^{2+}$ entry after cholesterol depletion.

Since Cholesterol seemed to act by enhancing PMN responses to S1P we assayed whether raft disruption would diminish SOCE in a GPC system where SOCE depends upon S1P synthesis. Moreover, we assessed whether excess S1P could restore normal GPC calcium entry. For MβCD treatment cells in Eppendorf tubes were prewarmed, spun down and resuspended in −BSA/—Ca buffer with 10 uM MβCD for 10 minutes. Cells were then spun and transferred to cuvettes with −BSA/—Ca buffer. Experiments were started and 100 nM PAF was added at 30 s. Calcium was added at 200 s. For S1P recovery 5 uM SIP was present in the cuvette. For controls (not shown) MβCD or DMSO treated cells were transferred to cuvettes with S1P (5 uM final) and Calcium was added at 200 sec. For blanks the cells were prewarmed and added to cuvettes after washing in −BSA/—Ca buffer. (FIG. 5)

Example 8

Figure 6:
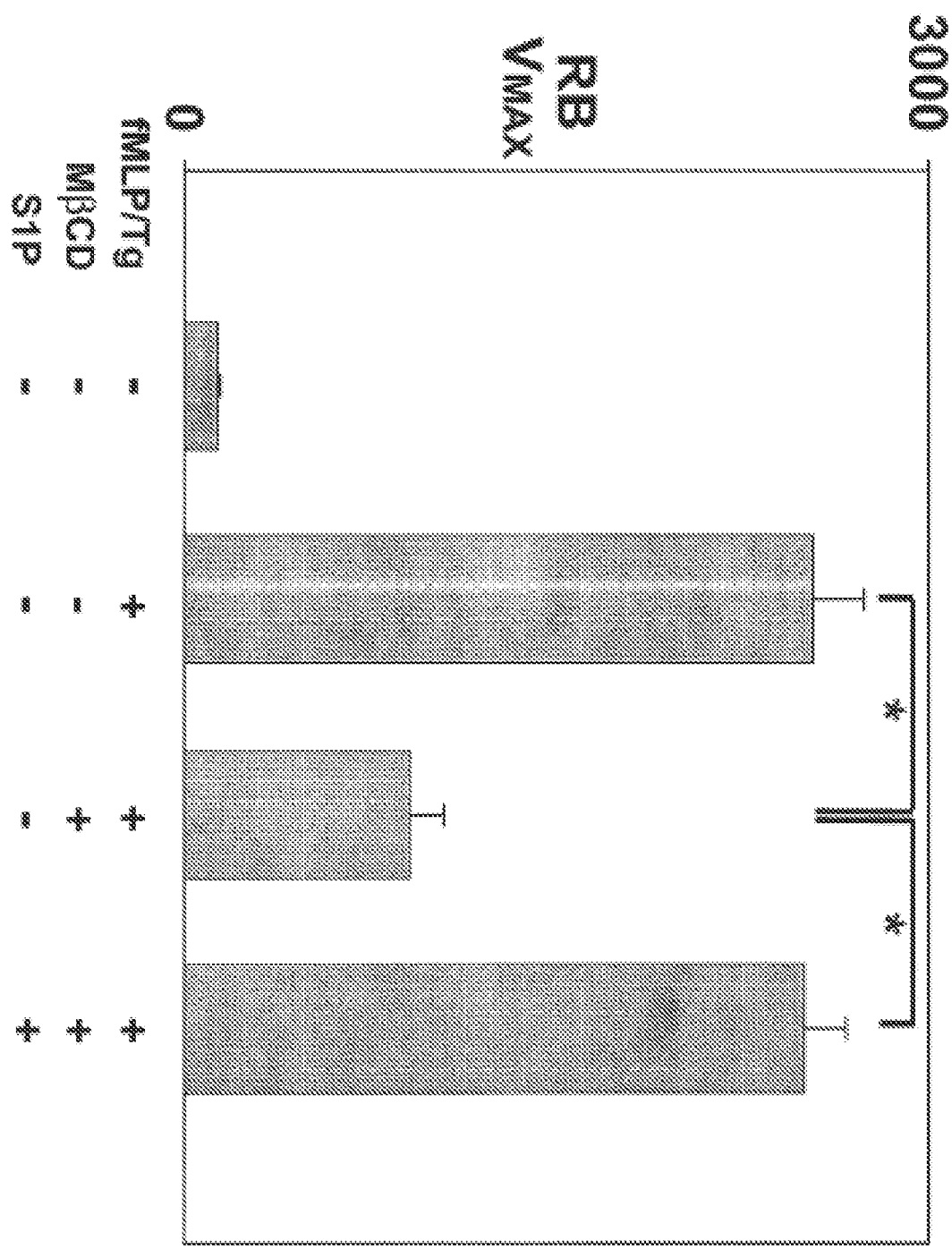
FIG. 6 is an assessment of whether S1P reverses the effects of cholesterol depletion by MBCD on respiratory burst.

Because S1P restored GPC Ca$^{2+}$ entry in PMN after cholesterol depletion we assessed whether it reversed the effects of cholesterol depletion by MβCD on respiratory burst. ANOVA (P=<0.001) showed that MβCD markedly suppressed RB responses to fMLP/Tg and that S1P restored RB to control levels (P<0.01 For all paired comparisons by Holm-Sidak method.) n=4-6. (FIG. 6)

Example 9

We examined whether cholesterol had any direct effect on calcium entry into human PMN and found that it had a direct dose-related response with a quite steep response curve. To insure this was a calcium channel related phenomenon we used lanthanum, a non-specific inhibitor of cationic channels. FIG. 19 shows that La$^{3+}$ (1 mM) almost totally inhibits cholesterol mediated PMN Ca$^{2+}$ influx. n=2-4 using PMN samples from different donors. These observations suggest that calcium entry is due to activation of specific ion transporters rather than a generalized loss of lipid bilayer barrier function.

Example 10

We looked further at the channel dependency of cholesterol-mediated PMN calcium entry by evaluating whether it was sensitive to dihydropyridines. SKF96365 (a non-specific dihydropyridine) blocked cholesterol-mediated PMN calcium entry with IC50~30 microM. L-type channel blockade (using verapamil) had no effect on cholesterol-mediated PMN calcium entry even at maximal concentrations (dose response curves not shown). These observations again suggest that increased membrane permeability to Ca$^{2+}$ is due to the activation of specific ion channels rather than to any generalized loss of lipid bilayer barrier function. FIG. 19 shows mean ±SE of 3-4 experiments per condition performed on different PMN isolates.

Example 11

Figure 7:
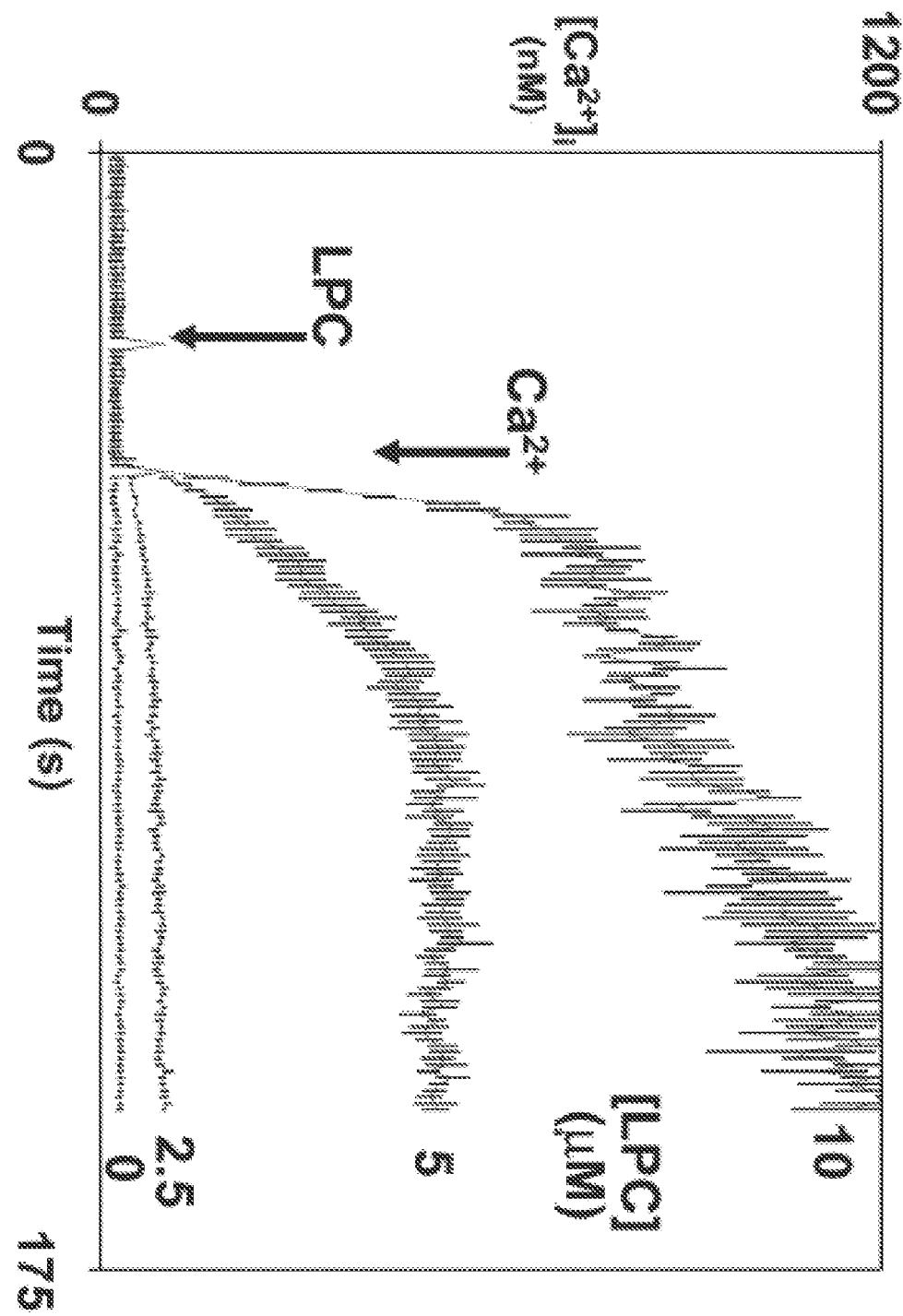
FIG. 7 shows the dose response of LPC to calcium influx in human neutrophils.

FIG. 7 depicts the dose response of LPC to Calcium influx in human neutrophils n=4-11. The Experiments are carried out in —Ca–BSA buffer in cuvettes. Cells loaded with fura2AM in +BSA+ca buffer. For MBCD treatment the cells are prewarmed, spun, resuspended in –BSA —Ca buffer, and treated with 10 mM MBCD for 10 minutes. For Cholesterol replenishment the cells after MBCD treatment are spun and supernatant taken off and cells resuspended in fresh –BSA and —Ca buffer and Cholesterol added at 3 ug/ml final conc in eppendorf tubes. After 1 minute incubation the cells are spun and transferred to cuvettes having –BSA-Calcium buffer. LPC at 5 uM is added at 30 sec and Calcium at 50 sec. Number of samples of each experiment: Blank 6; 2.5 uM LPC 4; 5 uM LPC 8; Lanthanum treatment 4; 10 uM LPC 4; MBCD treated cells 11; MBCD/Cholesterol 5.

Example 12

Figure 8:
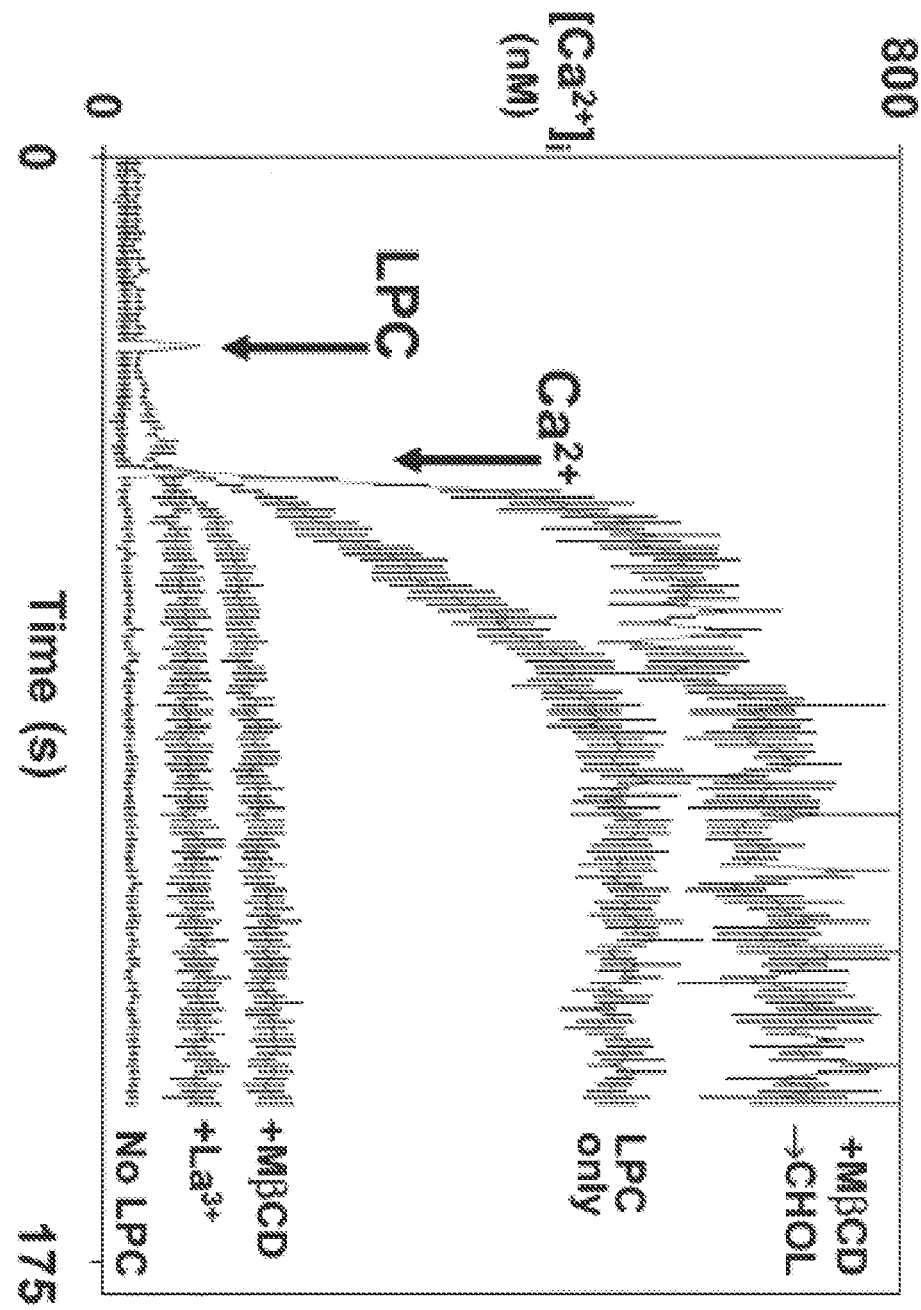
FIG. 8 shows the effect of cholesterol replenishment on MBCD treated cells and their rescue of LPC mediated calcium influx; the effect of lanthanum is also included.
Figure 9:
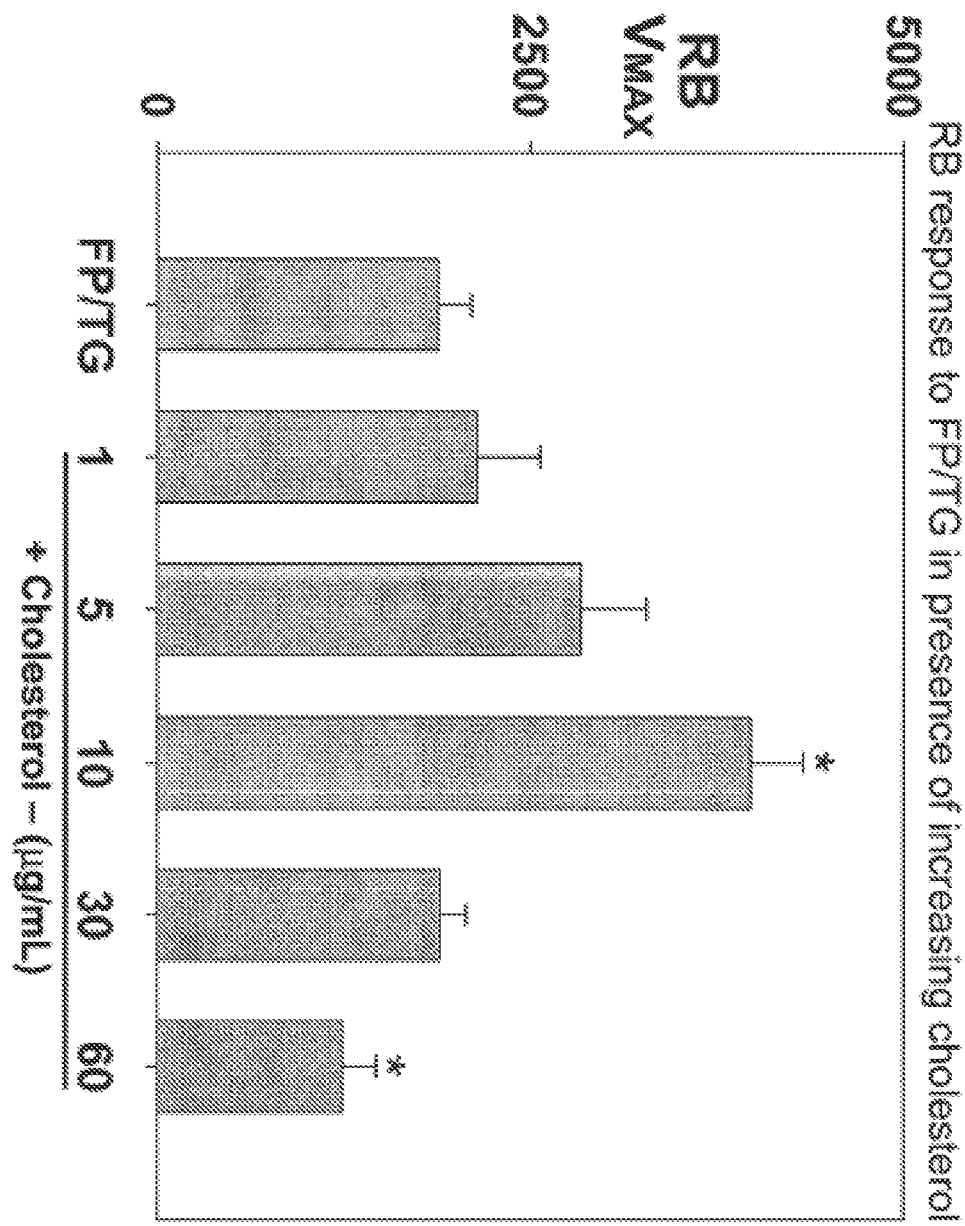
FIG. 9 demonstrates respiratory burst response to FP/TG in the presence of increasing cholesterol.
Figure 10:
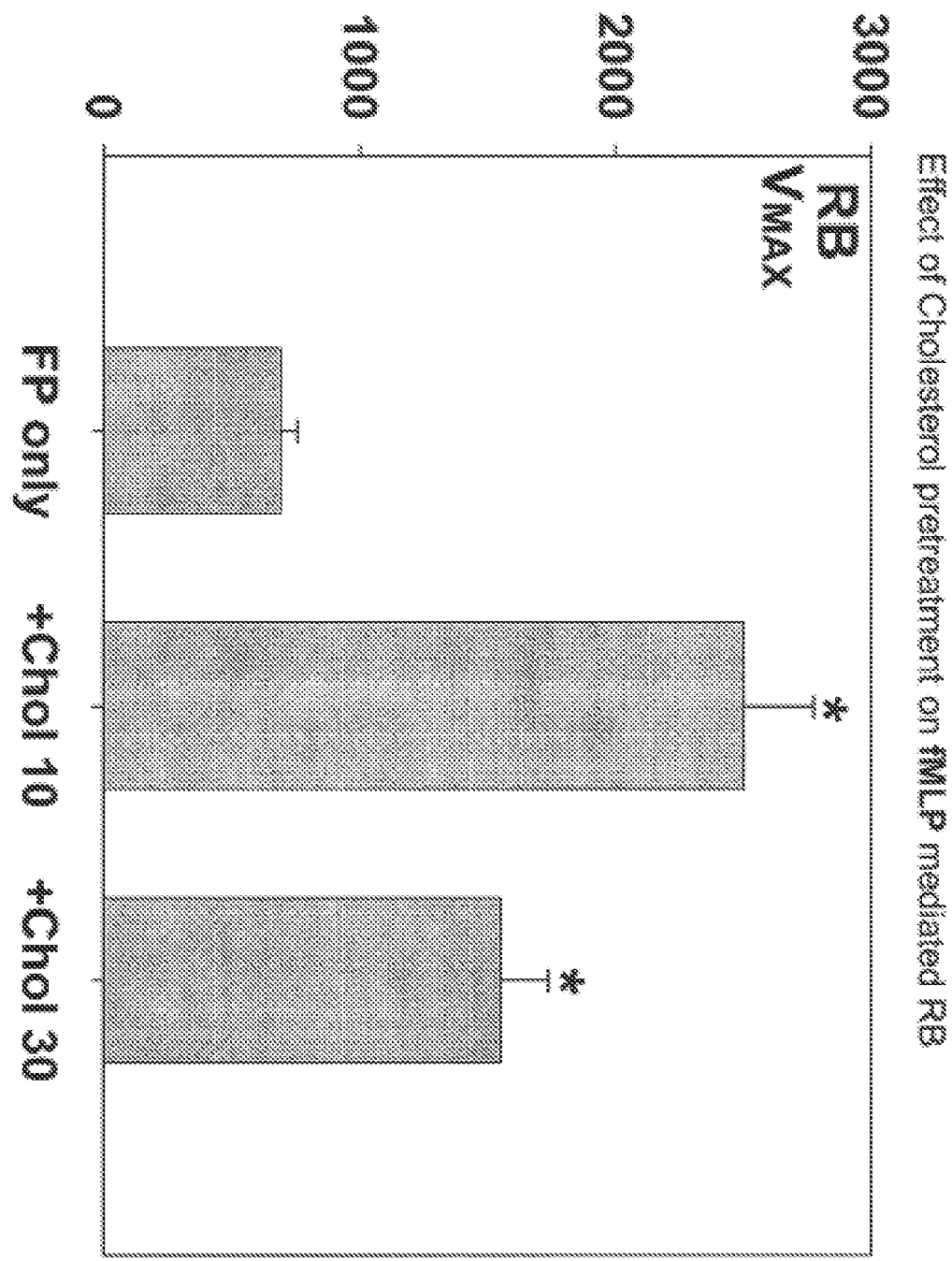
FIG. 10 illustrates the effect of cholesterol pretreatment on fMLP mediated RB.
Figure 20:
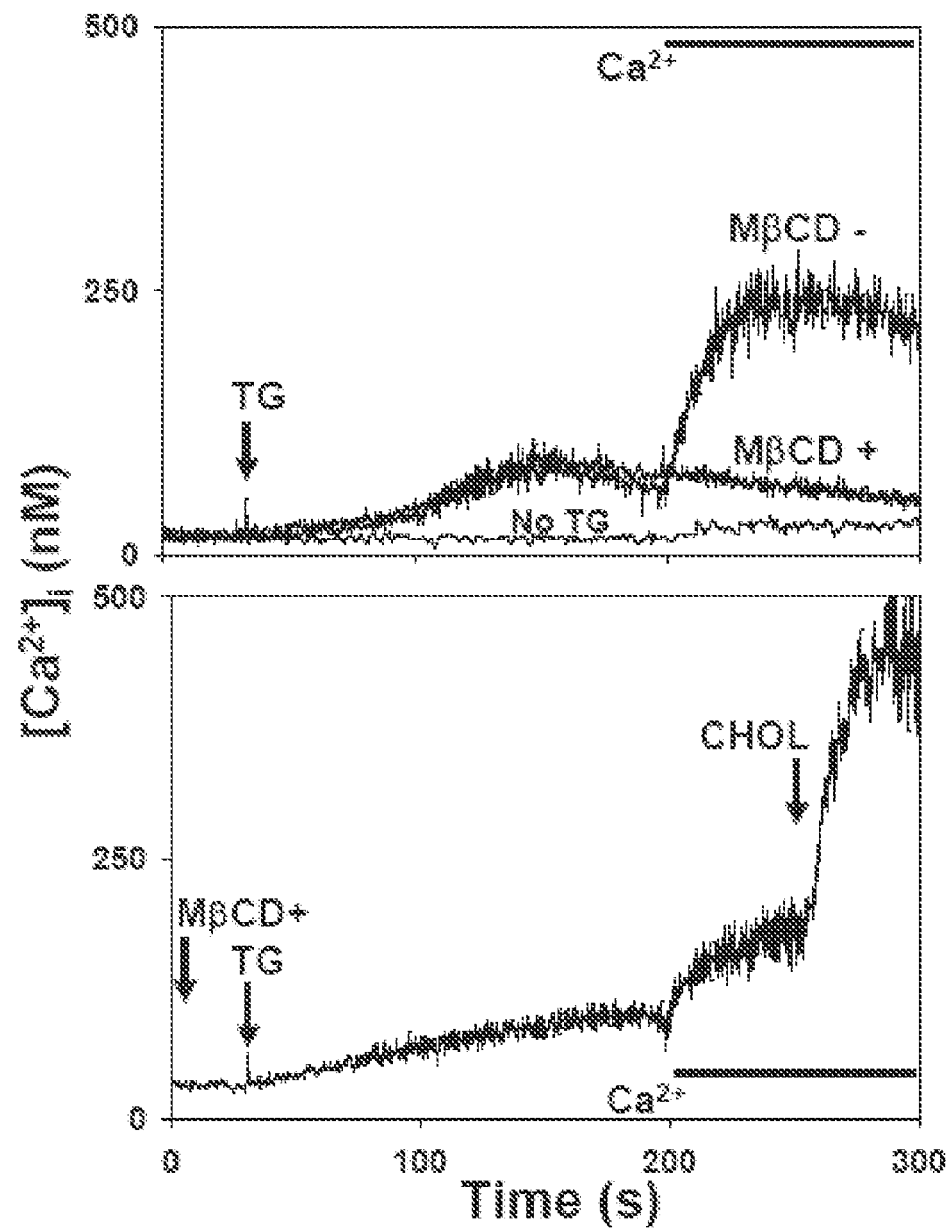
FIG. 20 demonstrates that cholesterol regulates Ca entry in response to thapsigargin (TG)
Figure 24:
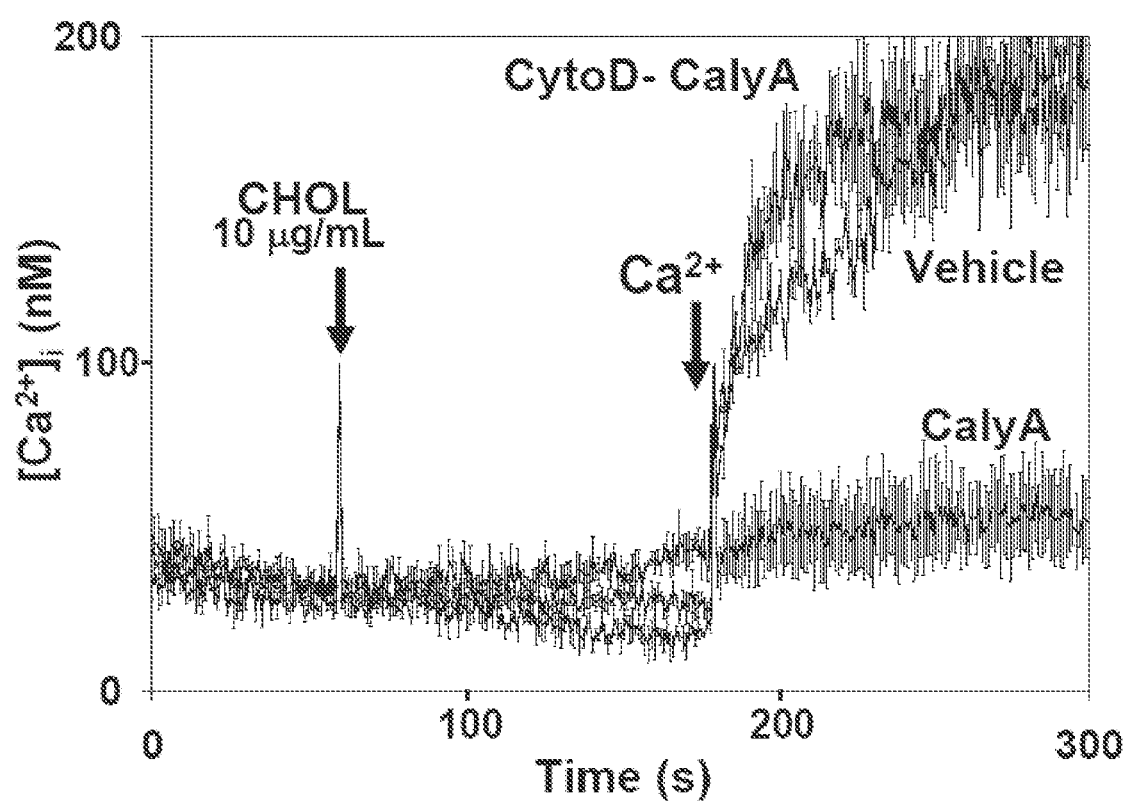
FIG. 24 shows the effect of CalyA on cholesterol-mediated calcium influx in human neutrophils and reversal of the effect by cytochalasin D pretreatment.

FIG. 8 depicts the effect of cholesterol replenishment on MBCD treated cells and their rescue of LPC mediated Calcium influx. Effect of Lanthanum is also included. FIG. 20 depicts cholesterol modulation of FP/Tg Respiratory Burst. FIG. 9 depicts RB Response to FP/TG in presence of increasing cholesterol. FIG. 24 depicts the effect of CalyA on Cholesterol mediated Calcium influx in human neutrophils and reversal of the effect of cytochalasin D pretreatment. n=3. –BSA —Ca buffer in cuvette. Cyto D pretreatment in eppendorf tubes at 2.5 uM for 15 min. Caly A 50 nM in cuvette. Cholesterol 10 ug/ml added at 60 sec. 1 mM $CaCl_2$ at 180 sec.

Example 13

FIG. 20 depicts the effects of cholesterol pretreatment on fMLP mediated respiratory burst in volunteer neutrophils (n=10). Cholesterol 10 ug/ml or 30 ug/ml in eppendorf tubes for 3 minutes in –BSA. FMLP (100 nM final) added at t=30 s. RB slope is calculated 1 minute after FP (ie during the interval t=85 s to t=95 s). * ANOVA P<0.001, Dunn's test P<0.05 for +10 or 30 uM cholesterol. Chol 10 vs 30=NS.

Example 14

Figure 11:
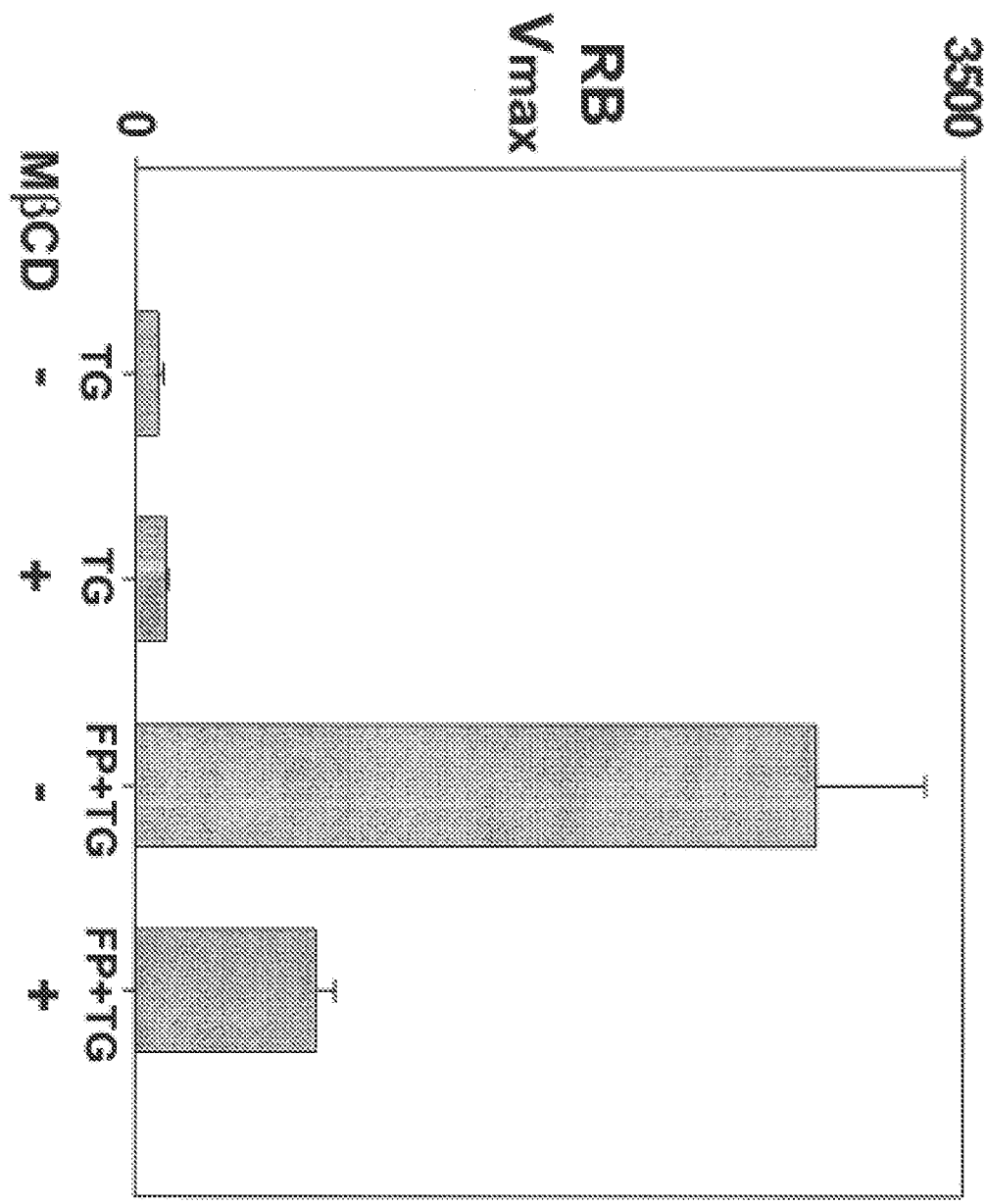
FIG. 11 shows that calcium-entry dependent PMN respiratory burst is raft dependent.

FIG. 11 shows that calcium-entry dependent PMN respiratory burst is raft dependent. MBCD depletion of raft cholesterol (10 mM/10 min) blocks RB in fMLP/TG (100 nM/1 uM) stimulated cells. n=3. Under these conditions RB is highly dependent on calcium entry, but we also have other controls (v.i.). Note RB depends not only on calcium entry (generated by thapsigargin—TG) but also on fMLP (which activates MAPK's).

Example 15

FIG. 12 depicts the rescue of calcium-entry dependent respiratory burst by cholesterol (30 ug/ml) on MBCD treated human neutrophils. The graph represents Vmax slopes values. n=2 for Blank, Cholesterol Blank and Cholesterol alone. The others are n=6. Both excess cholesterol and cholesterol depletion attenuate RB. After cholesterol depletion, restoration rescues RB.

Figure 13:
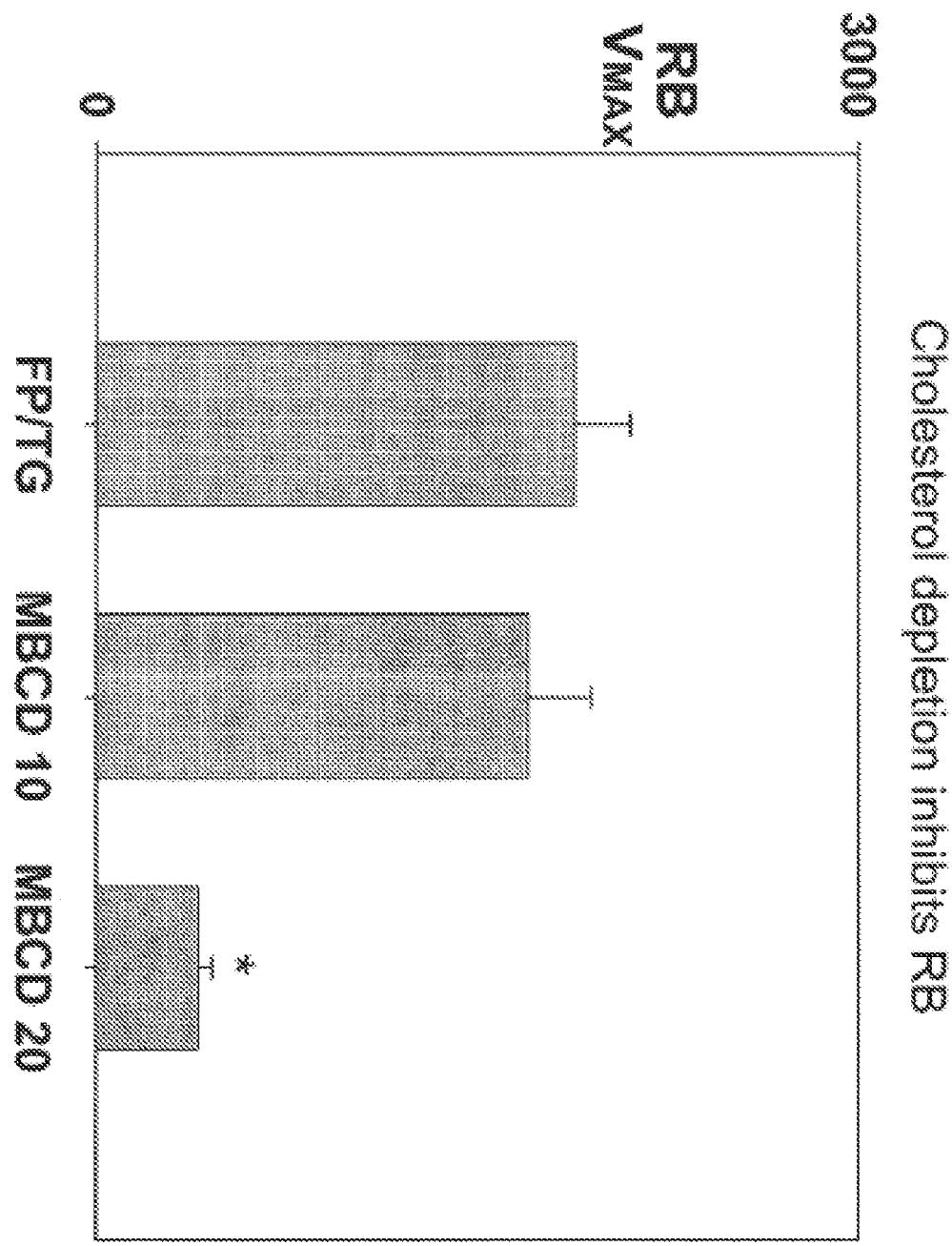
FIG. 13 shows that cholesterol depletion inhibits RB.

FIG. 13 demonstrates that cholesterol depletion inhibits RB. FIG. 14 represents the results of the evaluation of a large group of prospectively collected trauma patient plasma samples revealed that plasma sphingosine 1-phosphate levels are suppressed during the initial week after injury, when patients are at high risk for sepsis. Moreover, suppression of S1P levels was markedly greater in patients who developed sepsis than in those who do not. Patients who had plasma levels of S1P greater than 1 S.D. below matched volunteer plasma levels on admission had a median ICU length of stay of 11 days. Those whose levels were within 1 S.D. of 'normal' levels spent a median 4 days in the ICU. These data suggest S1P is critically important in the immune surveillance of sepsis.

Trauma patients not only have lower levels of circulating SIP, they also have lesser immune responses to SIP. FIG. 15 shows that neutrophils (PMN) mobilize less calcium on exposure to S1P than volunteer PMN. This effect dissipates over the week after injury. Diminished response to S1P in the presence of diminished presence of S1P suggests an additive, physical-chemical mechanism rather than an enzymatic or receptor based mechanism for this effect.

Example 16

Lipid raft fractions were isolated by ultracentrifugation from PMN treated with S1P, cholesterol or buffer only ("none"). Pretreatment with micromolar concentrations of cholesterol (in the absence of albumin) more than doubled the ratio of cholesterol to protein in the lowest density raft fractions, demonstrating that excess ("free") cholesterol can radically alter lipid raft environments. (FIG. 16) Of even more note, treatment with SIP resulted in even greater increases in cholesterol concentration in the lowest density raft fractions. Thus we see that environmental cholesterol and environmental sphingolipids interact to alter lipid raft composition, and as seen in the other studies, lipid raft function.

Examples 17-25

Materials

Cholesterol assay kits and Fura-2AM were purchased from Molecular Probes. Polyclonal rabbit anti-human TRPC1 antibodies as well as horseradish peroxidase-conjugated secondary antibodies were obtained from Santa Cruz Biotechnology. The ECL Western blotting detection reagents were purchased from Amersham. Protease inhibitor cocktail, Calpain inhibitor I, Optiprep (60% iodixanol in water, Nycomed), P-Nitrophenyl phosphate, Cholera Toxin B-peroxidase conjugates, water soluble cholesterol, Sphingosine-1-phosphate (SIP), platelet activating factor (PAF), n-formyl-met-leu-phe (fMLP) and methyl-β cyclodextrin (MβCD) and thapsigargin (TG) were purchased from Sigma Chemicals.

PMN Isolation

PMN were isolated from volunteers by venipuncture into heparinized (20 U/ml) tubes. Blood was spun (150 g×10 min) to remove platelet-rich plasma. Cells were then layered onto equal volumes of Polymorphoprep medium (Robbins Scientific, Sunnyvale, Calif.) and separated. PMN layers were removed and mixed with an equal volume of 0.45% NaCl solution to restore osmolarity for 5 minutes. Cells were washed, pelleted and resuspended in the indicated buffers.

Calcium Spectrofluorometry

PMN were suspended in HEPES buffer with 1 mM $CaCl_2$ and 0.1% BSA and incubated with 2 μg/mL fura-2AM for 30 minutes in the dark at 37° C. Cells were divided into aliquots ($2\times10^6$ PMN) and placed on ice in the dark. Prior to study, samples were warmed to 37°, centrifuged (4500 RPM, 5 sec) and supernatants removed. Pellets were resuspended in 200 μl of BSA-free and 'nominally calcium-free' HEPES buffer (with 0.3 mM EGTA) and finally injected into cuvettes containing 2.8 mL of the same buffer for study. Intracellular free calcium concentration ($[Ca2+]_i$) was determined from the fluorescence at 505 nm using 340/380 nm dual wavelength excitation. (Fluoromax-2, Jobin-SPEX, Edison, N.J.).

Respiratory Burst (RB)

RB was assessed in PMN suspensions. Briefly, $2 \times 10^6$ PMN were suspended in 3 ml of HEPES buffer with 0.1% BSA and 15 ng/ml of 1,2,3-dihydrorhodamine (DHR) added. Cells were studied at 37° C. with constant stirring using excitation at 488 nm and emission at 530 nm. RB was allowed to become linear and achieve maximal reaction rate (Vmax). The fluorescent intensity (FI) curve of oxidized DHR was compiled for 60 seconds during Vmax. Curve-fitting analysis was performed over the linear portion (Sigma-Plot 4.0, SPSS, Chicago, Ill.). Vmax was assessed as the first derivative of the fluorescent intensity in counts per second (CPS).

Lipid Raft Isolation

Rafts were prepared by an adaptation of the detergent-free methods of Macdonald, J. L. and Pike, L. J., "A simplified method for the preparation of detergent-free lipid rafts," J. Lipid Res. 46:1061-1067 (2005). After isolation from 2-3 normal volunteer donors, $5 \times 10^7$ PMN were divided into aliquots. Aliquots were treated at 37° C. with 10 µg/ml water-soluble cholesterol for 10 minutes, MβCD (10 µM/10 min) or with vehicle. All steps thereafter were performed on ice. Cells were spun and pellets resuspended in 1 ml of base buffer (20 mM Tris-HCl pH 7.8, 250 mM Sucrose, 1 mM $CaCl_2$ and 1 mM $MgCl_2$) containing protease inhibitor and 50 µg/ml calpain inhibitor 1. Cells were disrupted by passage through a 22 g 3" needle 10 times. Fragmented cells were sonicated $5 \times 20$ s, cooling the cells on ice between sonications. Lysates were centrifuged 1000×g for 10 min and supernatants were reserved. The cell pellets were resuspended in 1 ml base buffer with inhibitors and the sonication repeated. The two postnuclear supernatants were combined and an equal volume of 50% Optiprep added. Finally 4 mL of each lysate (1-2 mg protein) in 25% optiprep was placed in the bottom of the centrifuge tubes and 8 mL of a 20%-0% optiprep gradient was layered over it. Tubes were then centrifuged (52,000 g; 3 hours) and serial 670 µl fractions were collected from the top of the tube using careful pipetting.

Protein in each fraction was assayed by micro BCA assay method (Pierce, Rockford Ill.). Cholesterol was assayed using an Amplex Red cholesterol assay kit (Molecular Probes). Alkaline phosphatase was assayed using p-nitrophenyl phosphate as substrate.

Raft Fraction Localization with GM-1

Lipid rafts are rich in the ganglioside GM-1 and cholera toxin B (CTB) is a specific GM-1 ligand. We therefore confirmed the distribution of lipid rafts within the PMN fractions isolated above by GM-1 assays. Briefly, after treatments as described above, PMN were spun (450 g, 5 s). Cell pellets were suspended in 100 µl of PBS and incubated with 3 µl of CTB bound to horseradish peroxidase (CTB-HRP: 0.45 mg/ml CTB, 1 mg/ml HRP) for 30 min on ice. Cells were then washed to remove unbound CTB-HRP and processed to obtain raft fractions as above. Dot immunoassays were used to demonstrate the differential distribution of GM1 in density fractions. Briefly, 5 µl of each gradient fraction was applied to slot blots. Standard curves were created using known amounts of CTB-HRP. CTB-HRP conjugates were then visualized with ECL reagent and quantified on an Alpha Imager 3400 (Alpha Innotech).

Immunohistochemistry for GM-1

As noted above, GM-1 ganglioside is widely used as a marker in studies of lipid raft density and distribution. We studied the density and localization of GM-1 by immunohistochemistry in order to determine whether altered cholesterol content directly induced such changes in raft structure. Freshly isolated PMN were divided into aliquots of $1.5 \times 10^5$ cells and allowed to adhere for 20 minutes to chamber slides coated with 0.01% polylysine (Sigma). Slides were washed with buffer to remove non-adherent cells. Individual chambers were then flushed with 10 µg/ml cholesterol or with vehicle and cells were allowed to incubate for 5 minutes at room temperature. Slides were again washed with buffer. Slides were then stained with CTB-FITC (Sigma, 1:50 dilution in 1×PBS) for 30 minutes in the dark on ice. After labeling, cells were washed and then fixed using 2% paraformaldehyde in PBS for 10 min and washed 3× with PBS. Negative controls were created by pre-treating cells with non-fluorescent CTB prior to being stained with the CTB-FITC. Cells were imaged on a Zeiss Axiovision 200 fluorescent microscope using a 63× objective and Axiovert 4.5 software.

Western Blotting to Detect TRPC1 in Raft Fractions

TRPC1 is a prototypic calcium channel protein of the TRP family. PMN express multiple TRPC proteins that are known to traffic to the cell membrane during Ca entry. We therefore studied TRPC1 raft-trafficking in response to cholesterol as an initial proof of principle that raft cholesterol concentration might regulate the distribution of multiple $Ca^{2+}$-influx related proteins to or from the cell membrane. We analyzed 20 µl of each gradient fraction by electrophoresis on a SDS gel followed by Western blotting for TRPC1 protein. The primary rabbit anti-human TRPC1 antibody (Santa Cruz) was used at 1:1,600 dilution. Secondary goat anti-rabbit antibody was used at 1:16,000 dilution. An ECL Western blotting detection kit was used to develop the blots which were imaged as above.

Example 17

Figure 17:
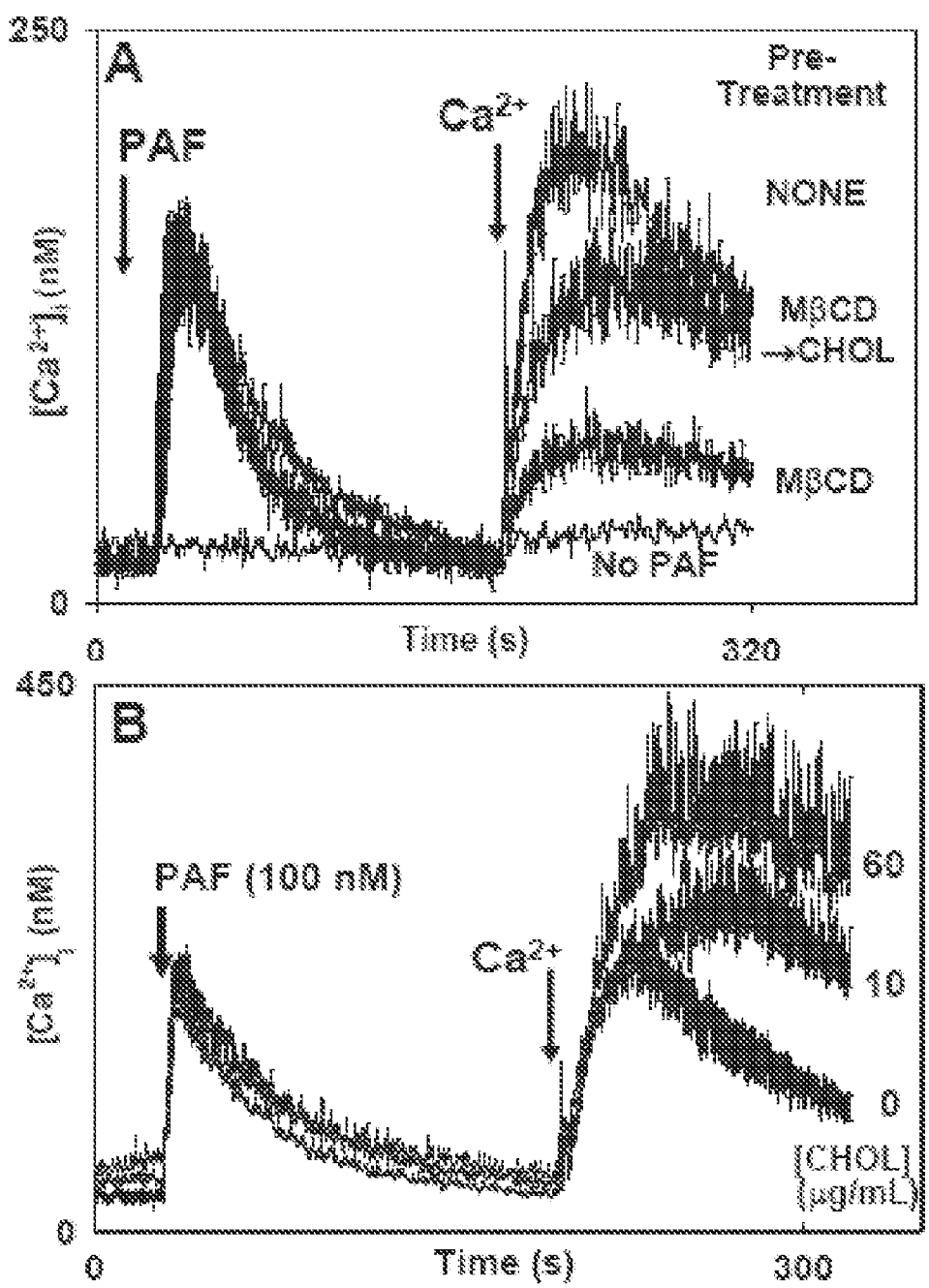
FIGS. 17 A and 17 B show that cholesterol restores SOCE after raft disruption.

Ligation of neutrophil G-protein coupled receptors (GPCR) by Platelet Activating Factor (PAF) depletes ER $Ca^{2+}$ stores. Store depletion then activates cellular $Ca^{2+}$ entry in a sphingosine kinase-dependent fashion. We studied whether one or both of these phases of calcium mobilization could be blocked by lipid raft disruption (FIG. 17A). When we used MβCD to remove cholesterol from and thus disrupt rafts we found that $Ca^{2+}$ entry was blocked by cholesterol sequestration and small amounts of cholesterol rescued $Ca^{2+}$ entry. Cholesterol depletion had no effect whatsoever on release of $Ca^{2+}$ from cell stores, demonstrating that the afferent arm of GPCR signaling here was not affected by rafts disruption.

To see if increased cholesterol bio-availability amplified $Ca^{2+}$ entry into normal cells, PMN were then stimulated by PAF with cholesterol present in the cuvette (FIG. 17B). Again, cholesterol had no effect upon $Ca^{2+}$ store mobilization, but even such brief exposure increased $Ca^{2+}$ entry. The data in FIGS. 17A and 17B confirm work showing that statin drugs and MβCD suppress $Ca^{2+}$ entry rather than release, but together they show that it is cholesterol bio-availability per se rather than "raft disruption" or the presence of statin drugs that modulates $Ca^{2+}$ flux.

Example 18

Since cholesterol availability modulated $Ca^{2+}$ entry we sought to determine whether this was specifically related to cholesterol incorporation into rafts. We therefore isolated PMN rafts after treatment with cholesterol or MβCD to raise or lower cholesterol bioavailability. No detergents were used in raft preparation. Raft fractions were identified by their high cholesterol and low protein contents, their high alkaline phosphatase activity (FIG. 18A) and the presence of GM-1 ganglioside (FIG. 18B). These experiments show that bio-available cholesterol is incorporated preferentially into the low density fractions displaying raft markers (FIG. 18C). Conversely, treatment of PMN with MβCD removed cholesterol from raft fractions with little effect on higher density fractions (FIG. 18C). The degree of cholesterol depletion by MβCD was similar to that seen in studies using whole cells, also suggesting MβCD specifically depletes raft cholesterol.

Example 19

Since cholesterol uptake into rafts augmented agonist-initiated $Ca^{2+}$ entry we studied whether cholesterol could stimulate $Ca^{2+}$ uptake directly. We found that cholesterol caused Ca entry without any antecedent release of calcium stores. This was best seen in albumin-free media, where immediate dose-dependent responses were seen (FIG. 19A). We used a standard battery of channel inhibitors to investigate this phenomenon further. $Ca^{2+}$ entry was inhibited by the inorganic channel blocker lanthanum ($La^{3+}$, 1 mM) showing that it is cation channel dependent. Similar $Ca^{2+}$ entry was seen in albumin containing media (0.1% BSA) but this required longer incubation, suggesting albumin-bound cholesterol desorbs onto cells gradually. To further delineate the type of cation channel(s) involved we then studied cholesterol mediated $Ca^{2+}$ uptake in the presence of L-type (verapamil—VER) and non-specific (SKF96365—SKF) calcium channel inhibitors (FIG. 19B). Dose response curves were created (not shown) but maximal activity was found at or near the expected concentrations based on prior publications. Non-specific $Ca^{2+}$ channel blockade (with SKF) quantitatively inhibited cholesterol-mediated $Ca^{2+}$ influx. As expected, L-type channel blockade (VER) had no effect at any concentration since PMN lack voltage gated calcium channels.

Example 20

Since cholesterol had no discernable effect on ER $Ca^{2+}$ store release in response to PAF we examined the possibility that could play a direct role in the regulation of store-operated $Ca^{2+}$ entry; a $Ca^{2+}$ entry mechanism that is completely independent of GPCR activation. To study this we used thapsigargin (TG). TG blocks ER $Ca^{2+}$ ATPase pumps, thus depleting ER $Ca^{2+}$ stores directly and causing calcium entry independent of GPCR activation. As with PAF mediated entry, we found that MβCD markedly inhibited TG initiated $Ca^{2+}$ entry (FIG. 20 upper panel). This inhibition was specific for MβCD's effect on cholesterol in that that the inhibition was immediately reversed and even overcome by cholesterol re-addition (FIG. 20, lower panel).

Example 21

Next we evaluated the functional relevance of cholesterol-mediated $Ca^{2+}$ influx. We studied a PMN model where RB depends entirely on extra-cellular calcium entry to see if RB would vary with the incorporation of cholesterol into rafts. First, we showed that cholesterol sequestration by MβCD inhibited RB (FIG. 21A, Column 4) and next that cholesterol replacement rescued RB from MβCD inhibition (FIG. 21A, Column 5). Thus we showed RB in this model depends on the presence of cholesterol in intact rafts.

Since RB was $Ca^{2+}$ entry and cholesterol dependent, and we knew $Ca^{2+}$ entry was cholesterol-dose dependent (FIG. 19A) we now investigated whether RB was directly cholesterol-dose dependent in this model. To do this, PMN were pre-incubated with MβCD, with vehicle or with varying concentrations of cholesterol to vary membrane raft cholesterol content (FIG. 21B). After the pre-incubation, RB was initiated using fMLP/Tg. Under these conditions we found clear suppression of RB by MβCD (FIG. 21B, Column 1) and dose-dependent augmentation of RB by the lower concentrations of cholesterol (FIG. 21B, Columns 3-5). Surprisingly however, a clear biphasic relationship emerged where increasing cholesterol concentrations decreased the degree of respiratory burst (FIG. 21B, Columns 6-7). High cholesterol concentrations have been shown to inhibit immune cell $Ca^{2+}$ mobilization in other systems. We now believe that these apparently inconsistent prior findings simply reflect the existence of optimal cholesterol concentrations for cell $Ca^{2+}$ uptake in specific models. In this model it appears that 10 μg/mL (~25 μM) external cholesterol yields optimal PMN oxidant production, suggesting this was the concentration at which ratios of cholesterol to other lipids were most favorable for assembling raft signaling complexes.

Figure 22:
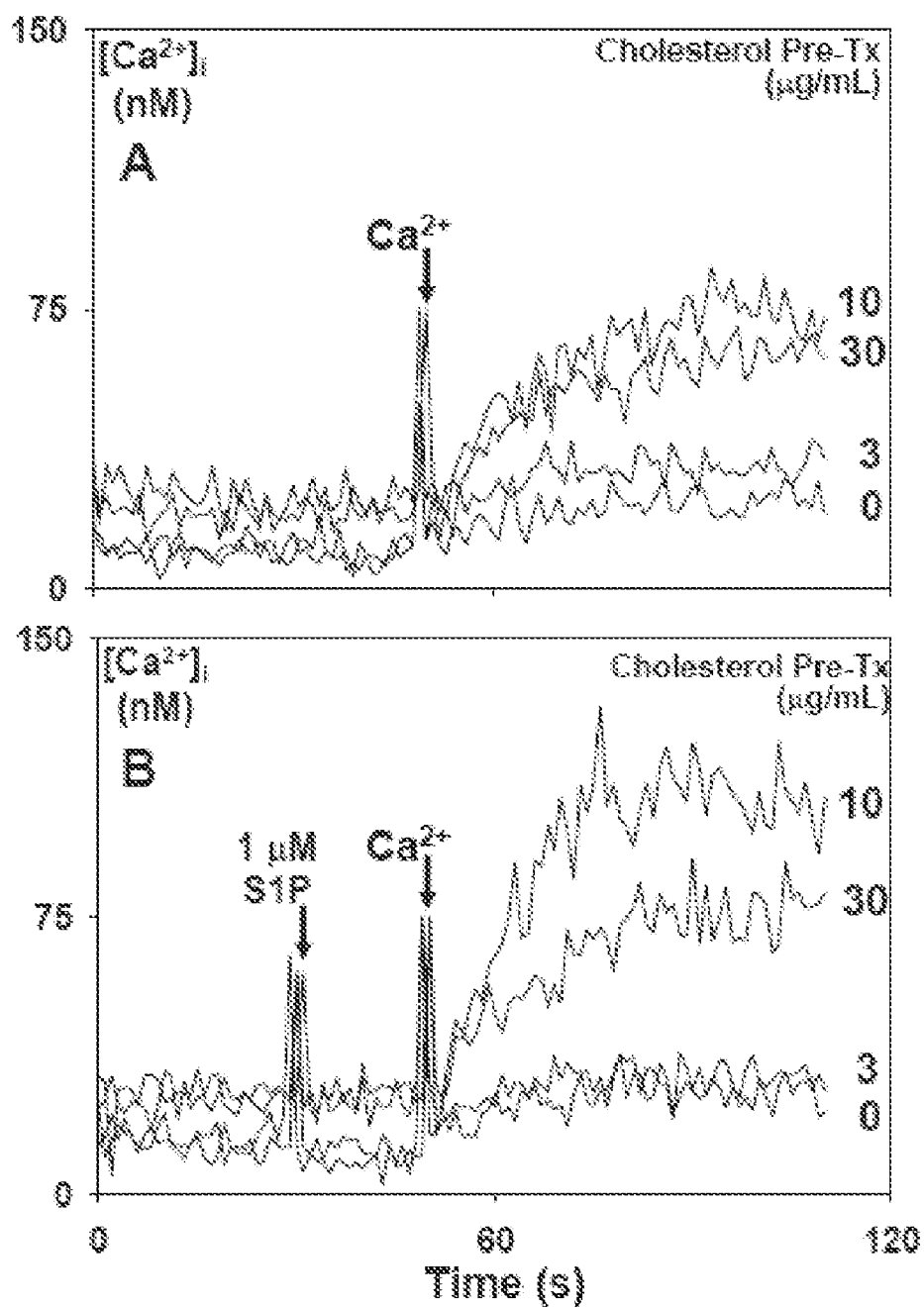
FIGS. 22 A and 22 B are studies verifying that the biphasic RB responses to cholesterol see specifically reflected cholesterol regulation of calcium entry.

To verify that the biphasic RB responses to cholesterol see specifically reflected cholesterol regulation of calcium entry we studied whether exposure to cholesterol concentrations above 10 μg/mL could suppress PMN $Ca^{2+}$ uptake. We found that this was true both for direct cholesterol stimulation of $Ca^{2+}$ entry (FIG. 22A) and for the synergistic combination of an ineffective concentration of sphingosine 1-phosphate (S1P) with cholesterol (FIG. 22B). This finding is of special significance since S1P synthesis links chemoattractant-induced store depletion to $Ca^{2+}$ influx.

Example 22

Figure 23:
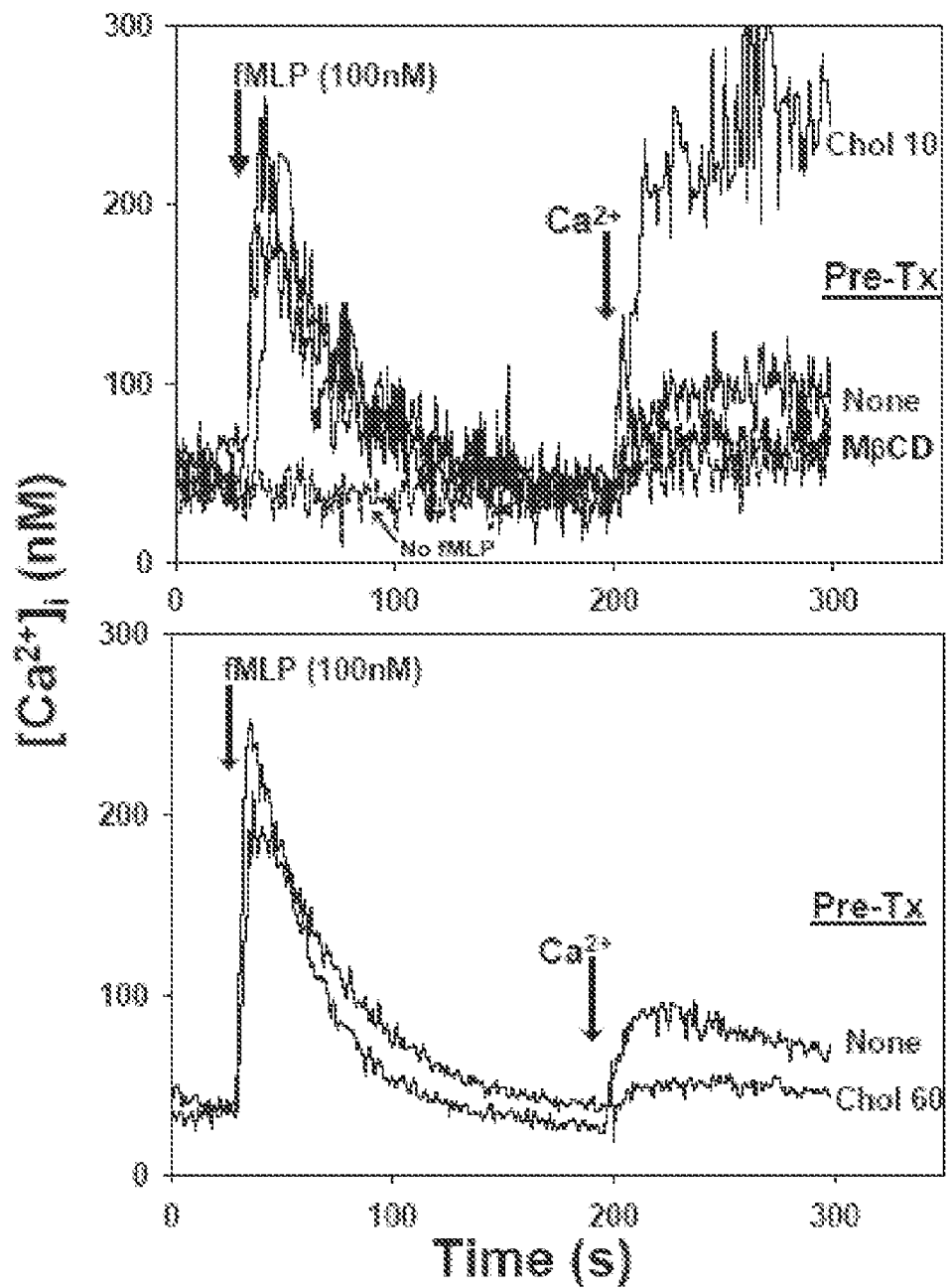
FIG. 23 demonstrates that cholesterol modulates $Ca^{2+}$ responses to FMLP.

To confirm that the effects of cholesterol on GPCR mediated $Ca^{2+}$ entry were generalized and not restricted to PAF we evaluated the effects of cholesterol on fMLP-mediated $Ca^{2+}$ entry. Consistent with PAF, fMLP-linked $Ca^{2+}$ entry responses were suppressed by MβCD and augmented by cholesterol (FIG. 23, upper panel). To further demonstrate that in our model GPCR-mediated $Ca^{2+}$ entry and RB were regulated in a coordinated and linked fashion, we studied the fMLP-mediated $Ca^{2+}$ entry responses of PMN at very high cholesterol concentrations. Again, we found that high cholesterol concentrations suppressed calcium entry (FIG. 23, lower panel).

Example 23

Calcium entry into PMN depends upon the redistribution of TRPC channel proteins. Calyculin A (CalyA) stabilizes cortical actin, forming a 'cortical bar' that prevents TRPC proteins from trafficking to membranes. CalyA also blocks $Ca^{2+}$ influx in response to $Ca^{2+}$-entry mobilizing signals. Cytochalasin D (CytoD) prevents actin assembly. Used with CalyA it prevents the formation of the 'cortical bar' which inhibits protein traffic to and from the cell membrane. CytoD therefore serves as a control to demonstrate the specificity of the CalyA effect for actin reorganization. We examined cholesterol mediated $Ca^{2+}$ influx in the presence of CalyA and found that it was abolished (FIG. 24). Consistent with our prior studies of TRPC trafficking in PMN, CytoD reversed the inhibition of cholesterol-induced $Ca^{2+}$ influx by CalyA. These experiments show cholesterol incorporation into rafts regulates $Ca^{2+}$ entry by mechanisms that are opposed by stabilizing cortical actin, which presumably prevents redistribution of proteins to and from the cell membrane. These findings are consistent with the concept that incorporation of cholesterol into rafts localizes $Ca^{2+}$ channels to the cell membrane.

Example 24

Figure 25:
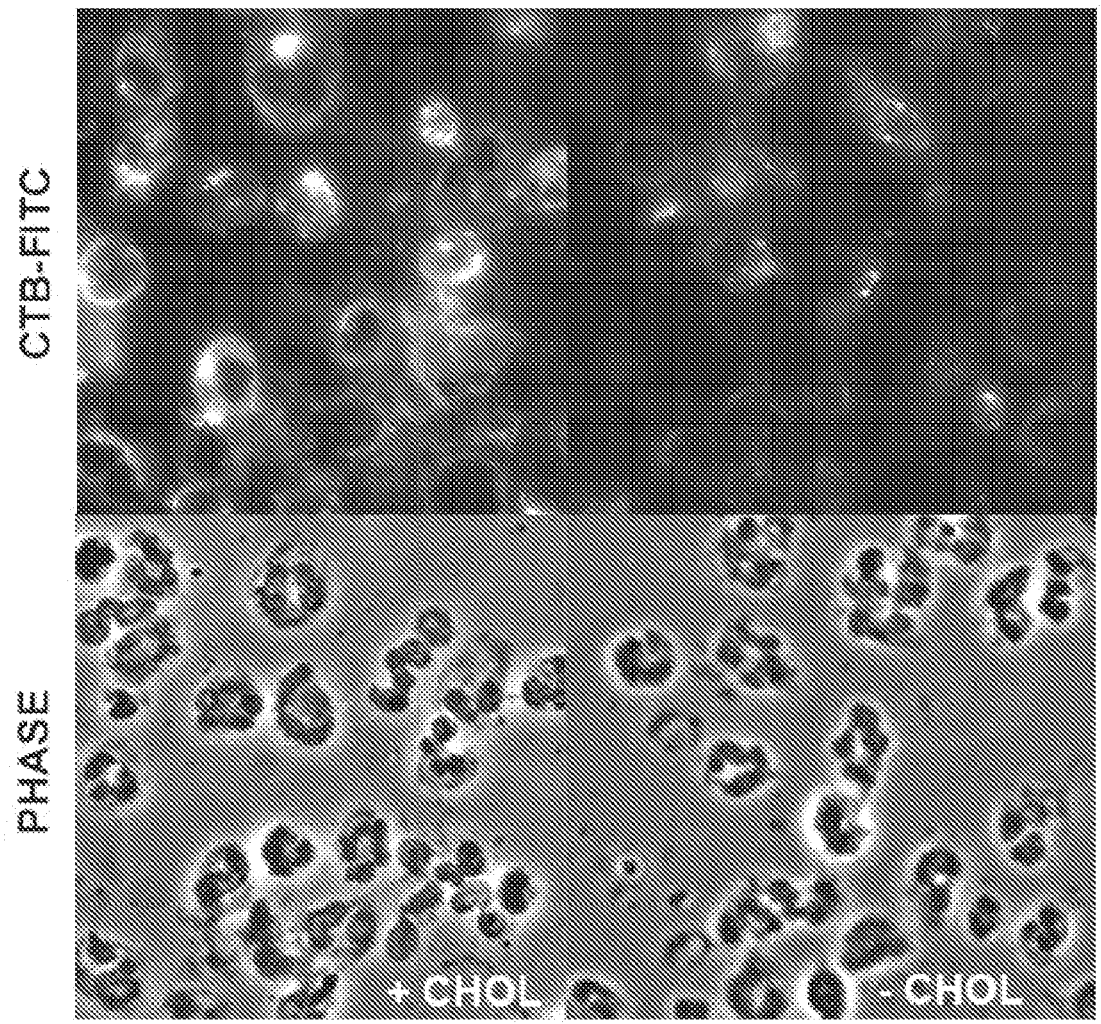
FIG. 25 shows the visualization of neutrophil lipid rafts by staining cells with cholera toxin B linked to fluorescein (CTB-FITC)

We knew exogenous cholesterol caused changes in raft composition, $Ca^{2+}$ entry and RB. We therefore questioned whether cholesterol enrichment of rafts might alter functionally important raft structural properties such as their coalescence into macrodomains or polarization to specific regions of the cell. We studied this with immunofluorescent microscopy, using FITC-CTB to bind GM-1 and visualize rafts directly. We found that exposure to free cholesterol (10 µg/mL) increased membrane GM-1 available for binding as well as causing brisk coalescence of GM-1 into polarized raft macrodomains (FIG. 25). Thus altering raft lipid composition by cholesterol addition changes raft structural characteristics known to be associated with function.

Example 25

Figure 18:
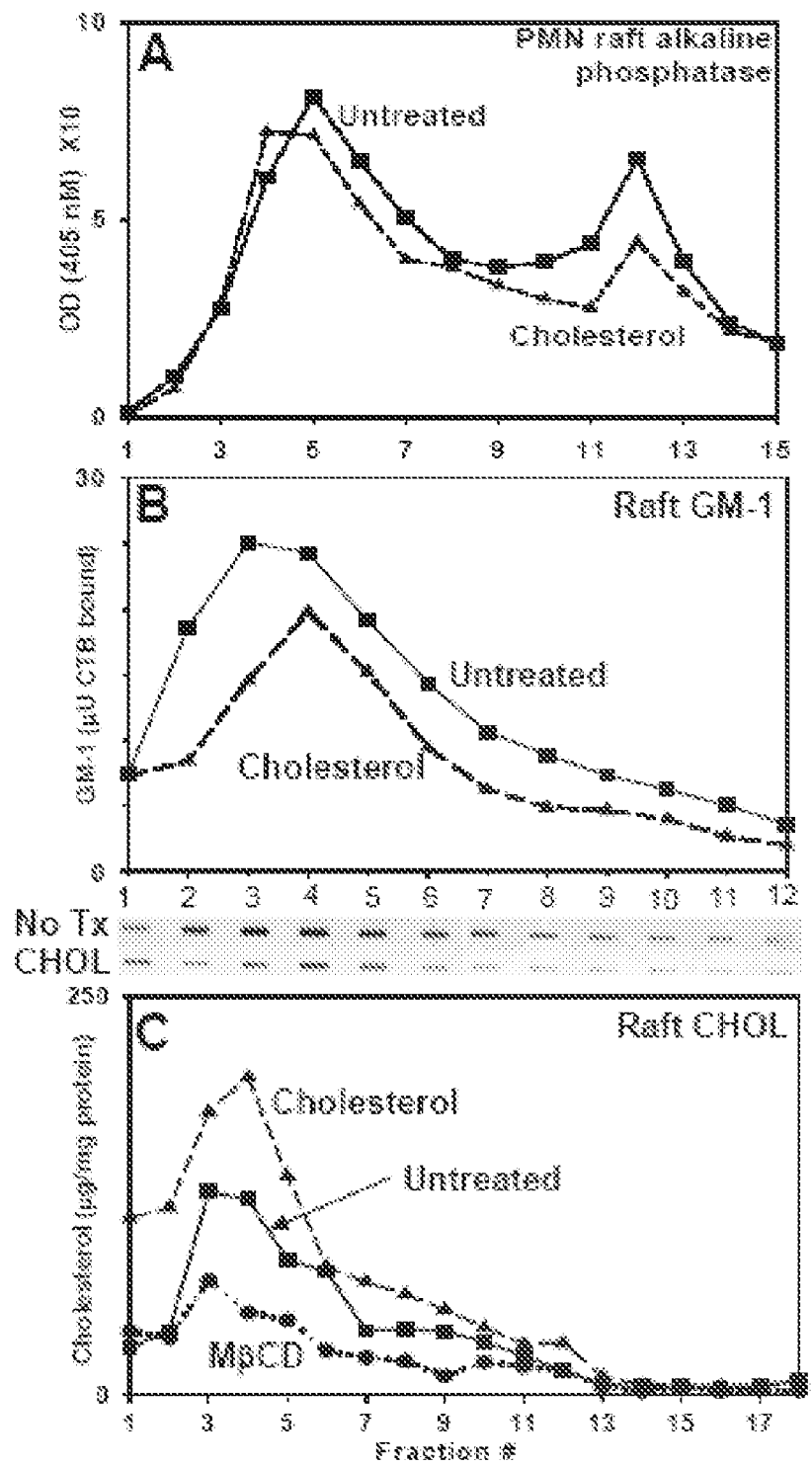
FIGS. 18 A, 18 B and 18 C depict fractionation for raft markers and cholesterol.

Thus cholesterol caused changes in raft composition, structure and function (FIGS. 18, 25). Also, regulation of $Ca^{2+}$ entry by cholesterol was dependent upon protein trafficking to the plasma membrane (FIG. 24). We therefore hypothesized that cholesterol might regulate trafficking of calcium channel proteins to rafts. The regulation of PMN $Ca^{2+}$ entry in vivo relies upon multiple channel proteins and these may show varied responses to changes in raft composition. Based upon our prior work and that of others however, we initially asked whether cholesterol might regulate raft-trafficking of TRPC1. TRPC1 is a prototypical TRPC protein that can both localize to rafts and transmit nonspecific $Ca^{2+}$ entry currents.

Figure 26:
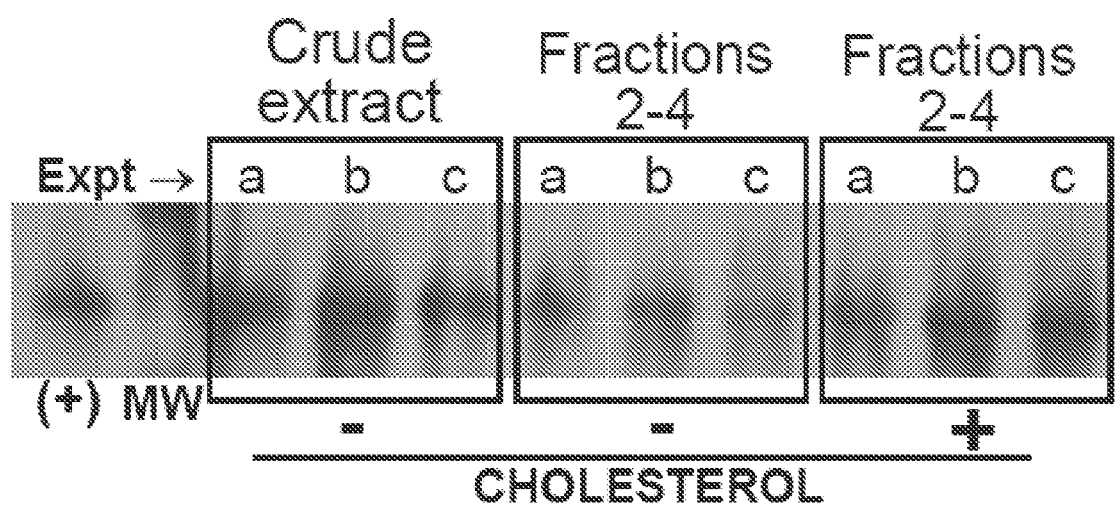
FIG. 26 shows the results of probing pooled, isolated normal PMN for raft TRPC1 with and without prior cholesterol treatment.

Using our fractionation methods, we noted that fractions 2-4 displayed the highest concentration of raft markers and exhibited maximal cholesterol incorporation (FIG. 18). We therefore used Western blots to probe for TRPC1 in fractions 2-4 of pooled normal volunteer PMN fractionated with or without prior incubation in 10 µg/mL cholesterol (FIG. 26). These studies demonstrate that pre-incubation of neutrophils in cholesterol increases the amount of TRPC1 protein in membrane lipid raft fractions.

Figure 27:
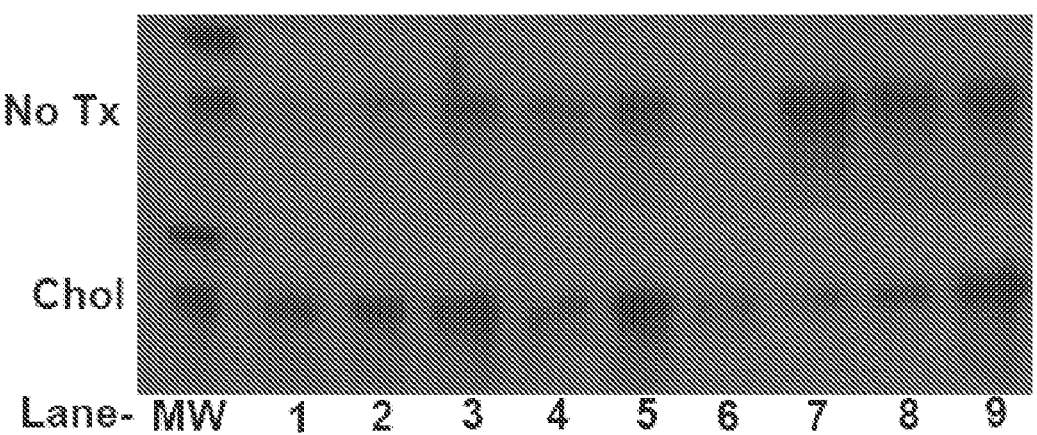
FIG. 27 shows the results of an assay for TRPC1 in individual raft fractions from concurrently treated and analyzed PMN specimens.

Subsequently, we sought to determine the source of the increased TRPC1 in the lipid raft fractions. Whole cell lysates from cholesterol treated and untreated cells were compared (not shown). No differences in global TRPC1 protein expression could be found between untreated PMN and PMN exposed either to cholesterol or to MβCD for 10 minutes. Since the events leading to calcium entry are very rapid, later time points were not studied. Finally, we assayed TRPC1 in individual raft fractions from concurrently treated and analyzed PMN specimens (FIG. 27). We found that cholesterol treatment caused redistribution of the TRPC1 signal from higher density fractions into the raft fractions (FIG. 27). Thus a redistribution of TRPC1 occurs in response to cholesterol treatment which appears to reflect trafficking of the protein to raft fractions rather than de novo synthesis.

The foregoing examples and description of the preferred embodiments should be taken as illustrating, rather than as limiting the present invention as defined by the claims. As will be readily appreciated, numerous variations and combinations of the features set forth above can be utilized without departing from the present invention as set forth in the claims. Such variations are not regarded as a departure from the spirit and scope of the invention, and all such variations are intended to be included within the scope of the following claims.

What is claimed is:

1. A method for suppressing an inflammatory cell response in a patient comprising administering to a patient suffering from an inflammatory response a non-statin agent in an amount to lower the patient's plasma concentration of free cholesterol to a level that inhibits $Ca^{2+}$-entry dependent inflammatory cellular function, so that said inflammatory cell response is suppressed, wherein the non-statin agent is methyl-beta cyclodextrin, and wherein said inflammatory response is caused by a hyperimmune or autoimmune response in said patient.

2. The method of claim 1, wherein the agent enhances the activity of an enzyme involved in the metabolism of the free cholesterol.

3. The method of claim 1, wherein the hyperimmune or autoimmune response is related to a disorder of systemic inflammation after trauma, injury or sepsis, transplant rejection, atherosclerosis, neointimal hyperplasia, rheumatoid arthritis, inflammatory bowel disease, Addison's disease, multiple sclerosis, or psoriasis.

4. The method of claim 1, wherein the agent is administered to the patient orally, intravenously or parenterally.

5. The method of claim 1, wherein the agent further comprises a pharmaceutically acceptable carrier.

* * * * *